(12) United States Patent
Han

(10) Patent No.: US 10,772,576 B2
(45) Date of Patent: Sep. 15, 2020

(54) X-RAY IMAGING APPARATUS AND CONTROL METHOD THEREOF

(71) Applicant: SAMSUNG ELECTRONICS CO., LTD., Suwon-si, Gyeonggi-do (KR)

(72) Inventor: Jong Chul Han, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/037,315

(22) Filed: Jul. 17, 2018

(65) Prior Publication Data

US 2019/0059829 A1 Feb. 28, 2019

(30) Foreign Application Priority Data

Aug. 22, 2017 (KR) .................. 10-2017-0106087

(51) Int. Cl.
*A61B 6/00* (2006.01)
*A61B 6/03* (2006.01)
(Continued)

(52) U.S. Cl.
CPC ............. *A61B 6/032* (2013.01); *A61B 6/025* (2013.01); *A61B 6/06* (2013.01); *A61B 6/08* (2013.01);
(Continued)

(58) Field of Classification Search
CPC ................................ A61B 6/032; A61B 6/469
See application file for complete search history.

(56) References Cited

U.S. PATENT DOCUMENTS

2008/0101536 A1 5/2008 Sendai
2014/0119623 A1 5/2014 Mostafavi et al.
(Continued)

FOREIGN PATENT DOCUMENTS

DE 19802499 7/1999
JP 2013-81527 5/2013
(Continued)

OTHER PUBLICATIONS

International Search Report and Written Opinion of the International Searching Authority dated Dec. 31, 2018 in International Patent Application No. PCT/KR2018/009619.
(Continued)

*Primary Examiner* — Dani Fox
(74) *Attorney, Agent, or Firm* — Staas & Halsey LLP

(57) ABSTRACT

An X-ray imaging apparatus and control method thereof to prevent an error in the center of rotation of an X-ray source and degradation of resolution in a depth direction. The X-ray imaging apparatus comprises an X-ray source configured to irradiate X-rays, a sensor configured to obtain a distance between the X-ray source and a subject, a display configured to display a graphical object in association with the subject, an input configured to receive a designation of a region of interest of the subject through the graphical object, and a controller configured to obtain a thickness of the subject based on the distance between the X-ray source and the subject, determine a center of rotation to be set for the X-ray source based on the designation of the region of interest and the thickness of the subject, and control a movement of the X-ray source to set the center of rotation.

20 Claims, 25 Drawing Sheets

(51) Int. Cl.
  *G01B 11/02*   (2006.01)
  *G01B 11/06*   (2006.01)
  *A61B 6/02*    (2006.01)
  *A61B 6/06*    (2006.01)
  *A61B 6/08*    (2006.01)

(52) U.S. Cl.
  CPC ............ *A61B 6/4464* (2013.01); *A61B 6/465* (2013.01); *A61B 6/469* (2013.01); *A61B 6/54* (2013.01); *A61B 6/545* (2013.01); *A61B 6/588* (2013.01); *A61B 6/589* (2013.01); *G01B 11/026* (2013.01); *G01B 11/06* (2013.01)

(56) References Cited

U.S. PATENT DOCUMENTS

| | | |
|---|---|---|
| 2016/0019701 A1 | 1/2016 | Visser et al. |
| 2016/0088288 A1 | 3/2016 | Liu et al. |
| 2017/0055936 A1 | 3/2017 | Okuno et al. |
| 2017/0165501 A1 | 6/2017 | Rapaka et al. |
| 2018/0325486 A1* | 11/2018 | Kim .................. A61B 6/54 |

FOREIGN PATENT DOCUMENTS

| | | |
|---|---|---|
| KR | 10-2016-0026197 | 3/2016 |
| KR | 10-2016-0069434 | 6/2016 |

OTHER PUBLICATIONS

Extended European Search Report dated Jun. 15, 2020 in European Patent Application No. 18847342.5.

\* cited by examiner

X-RAY IMAGING APPARATUS AND CONTROL METHOD THEREOF

CROSS-REFERENCE TO RELATED APPLICATION

This application is based on and claims priority under 35 U.S.C. § 119 to Korean Patent Application No. 10-2017-0106087 filed on Aug. 22, 2017, in the Korean Intellectual Property Office, the disclosure of which is incorporated herein by reference in its entirety.

BACKGROUND

1. Field of the Invention

The present disclosure relates to an X-ray imaging apparatus and control method thereof for obtaining tomograms.

2. Discussion of Related Art

X-ray imaging apparatuses are devices for allowing the user to see an internal structure of a subject by irradiating X-rays to the subject and analyzing X-rays that have passed through the subject. X-ray transmittance depends on the tissue of a subject, so the internal structure of the subject may be imaged using an attenuation coefficient quantified from the X-ray transmittance.

Especially, when tomosynthesis equipment is used, not only two dimensional projection images but also three dimensional volume data and tomograms can be obtained, so that legions can be examined from various angles.

SUMMARY OF THE INVENTION

The present disclosure provides an X-ray imaging apparatus and control method thereof, capable of preventing occurrence of an error in the center of rotation of an X-ray source and the resultant degradation of resolution in a depth direction by measuring thickness of a subject and determining the center of rotation taking into account the thickness of the subject and a region of interest designated by the user.

In accordance with an aspect of the present disclosure, an X-ray imaging apparatus comprises: an X-ray source configured to irradiate X-rays; a sensor configured to obtain a distance between the X-ray source and a subject; a display configured to display a graphical object in association with the subject; an input configured to receive a designation of a region of interest of the subject through the graphical object displayed on the display; and a controller configured to obtain a thickness of the subject based on the distance between the X-ray source and the subject, determine a center of rotation of the X-ray source based on the designation of the region of interest of the subject received through the input and the thickness of the subject, and control a movement of the X-ray source to set the determined center of rotation of the X-ray source.

The sensor may comprise at least one of a stereo camera, a single camera, a depth camera, a photo sensor, an ultrasonic sensor, and a laser sensor.

The controller may be configured to obtain the thickness of the subject based on the distance between the X-ray source and the subject and a distance between the X-ray source and an X-ray detector.

The sensor may be further configured to detect the distance between the X-ray source and the X-ray detector.

The display may be configured to display the distance between the X-ray source and the subject and the thickness of the subject.

The display may be configured to display the graphical object in association with the subject to be proportional to the thickness of the subject.

The controller may be configured to determine a position of the region of interest in a direction of thickness based on a relationship between a designated position of the region of interest on the graphical object and the thickness of the subject, and determine the determined position in the direction of thickness as the center of rotation.

The controller may be configured to set a center of the subject in a direction of thickness to be the center of rotation of the X-ray source, before the designation of the region of interest, and the display may be configured to display information regarding a position of the set center of rotation on the graphical object.

The display may be configured to display a previously captured tomogram of the subject on the graphical object.

The X-ray source may comprise a collimator configured to adjust an X-ray irradiation area and a collimator lamp configured to irradiate visible rays into the X-ray irradiation area.

The sensor may be further configured to obtain a camera image having a guide line formed by the visible ray marked on the subject.

The sensor may be configured to obtain a correlated image using template matching, determine a position of a center of the guide line in the camera image based on the correlated image, and obtain the distance between the X-ray source and the subject based on the position of the center of the guide line.

In accordance with another aspect of the present disclosure, a control method of an X-ray imaging apparatus comprises obtaining thickness of a subject and displaying a graphical object in association with the subject.

The control method includes receiving a designation of a region of interest of the subject through the graphical object displayed by the displaying; determining a center of rotation to be set for an X-ray source based on the designation of the region of interest and the thickness of the subject obtained; and controlling a movement of the X-ray source to set the center of rotation determined by the determining.

The obtaining of the thickness of the subject may comprise using a sensor including at least one of a stereo camera, a single camera, a depth camera, a photo sensor, an ultrasonic sensor and a laser sensor to obtain the distance between the X-ray source and the subject.

The thickness of the subject is obtained based on the distance between the X-ray source and the subject and a distance between the X-ray source and an X-ray detector.

The control method may further comprise: displaying the distance between the X-ray source and the subject and the thickness of the subject.

The displaying of the graphical object in association with the subject may comprise displaying the graphical object to be proportional to the thickness of the subject.

The determining of the center of rotation of the X-ray source may comprise determining a position of the region of interest in a direction of thickness based on a relationship between the position of the region of interest which is designated on the graphical object and the thickness of the subject, and determining the determined position in the direction of thickness as the center of rotation.

The control method may further comprise: setting a center of the subject in a direction of thickness to be the center of rotation of the X-ray source, before the designation of the region of interest is designated; and displaying information regarding a position of the set center of rotation on the graphical object.

The graphical object displayed in association with the subject may comprise a previously captured tomogram of the subject.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
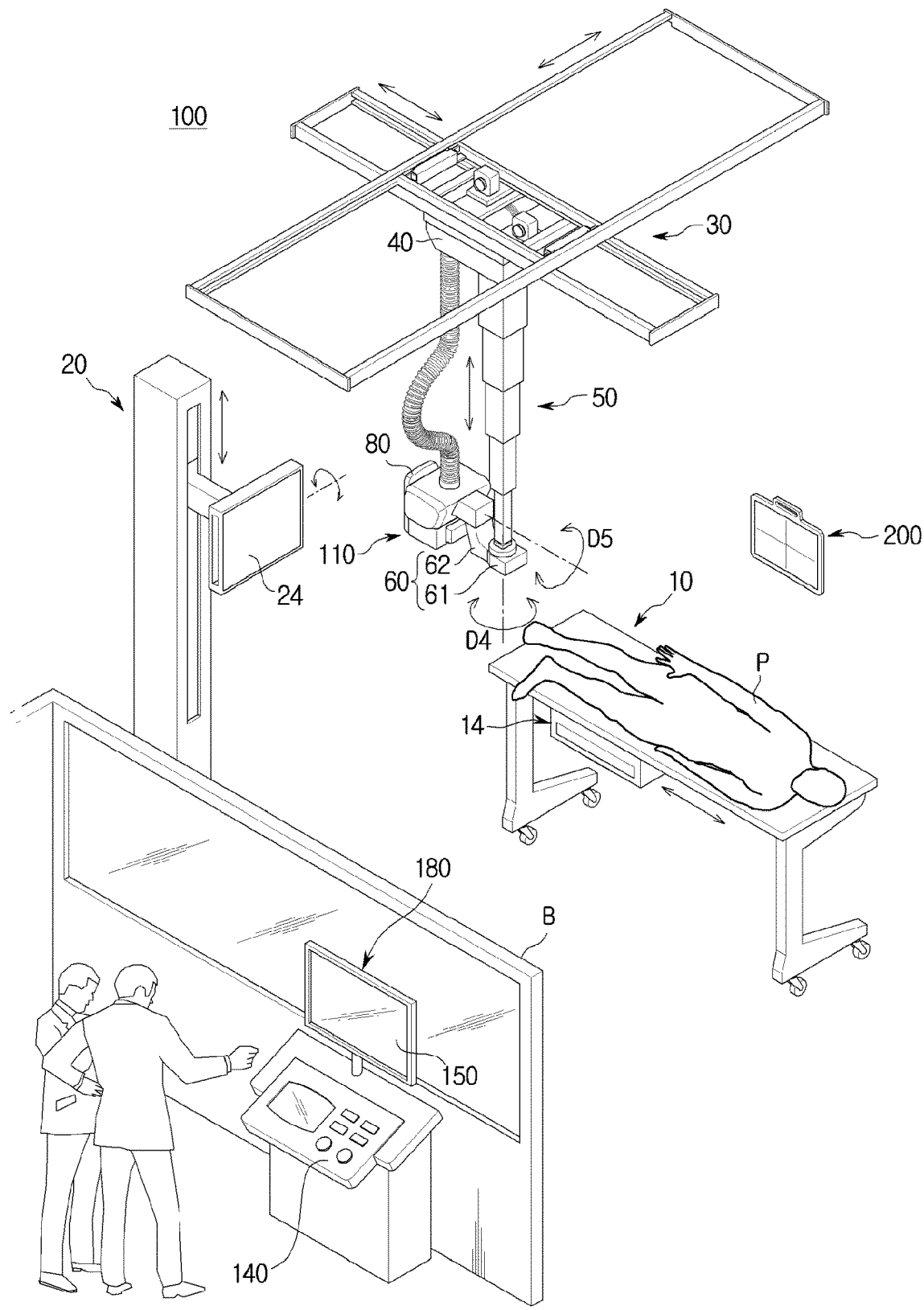
FIG. 1 is an external view illustrating a configuration of an X-ray imaging apparatus, according to an embodiment of the present disclosure.

Like numerals refer to like elements throughout the specification. Not all elements of embodiments of the present disclosure will be described, and description of what are commonly known in the art or what overlap each other in the embodiments will be omitted. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

It will be further understood that the term "connect" or its derivatives refer both to direct and indirect connection, and the indirect connection includes a connection over a wireless communication network.

The term "include (or including)" or "comprise (or comprising)" is inclusive or open-ended and does not exclude additional, unrecited elements or method steps, unless otherwise mentioned.

Throughout the specification, when it is said that a member is located "in front of" or "in the back of" another member, it implies not only that the member is located adjacent to the other member but also that a third member exists between the two members.

It is to be understood that the singular forms "a," "an," and "the" include plural references unless the context clearly dictates otherwise.

Reference numerals used for method steps are just used to identify the respective steps, but not to limit an order of the steps. Thus, unless the context clearly dictates otherwise, the written order may be practiced otherwise.

Embodiments of an X-ray imaging apparatus and control method thereof will now be described in detail with reference to accompanying drawings.

FIG. 1 is an external view illustrating a configuration of an X-ray imaging apparatus, according to an embodiment of the present disclosure.

Referring to FIG. 1, a guide rail 30 may be installed on the ceiling of an examination room where an X-ray imaging apparatus 100 is placed, and an X-ray source 110 linked to a moving carriage 40 that moves along the guide rail 30 may be moved to a position corresponding to a subject P.

The moving carriage 40 and the X-ray source 110 may be linked through a foldable post frame 50 to adjust the altitude (height) of the X-ray source 110.

A rotary joint 60 is arranged between the X-ray source 110 and the post frame 50. The rotary joint 60 may include a first rotary joint 61 coupled to the post frame 50 and a second rotary joint 62 coupled to the X-ray source 110.

The first rotary joint 61 may be rotated in a fourth direction D4 and the second rotary joint 62 may be rotated in a fifth direction D5. By rotating the second rotary joint 62 in the fifth direction D5, a tilt angle or a rotation angle of the X-ray source 110 may be adjusted.

The X-ray source 110 may be moved automatically or manually. In the former case, the X-ray imaging apparatus 100 may further include a driver, such as a motor to provide power to move the X-ray source 110.

A workstation 180 may be provided in the space separated by a blackout curtain B from the space where the X-ray source 110 is placed. The workstation 180 may be equipped with an input 140 for receiving commands from the user and a display 150 for displaying information.

The input 140 may receive commands for setting an imaging protocol, an X-ray irradiation condition, X-ray irradiation timing, and/or a region of interest and/or for controlling the position of the X-ray source 110. The input 140 may include a keyboard, a mouse, a touch panel, a voice recognizer, and/or the like. For example, the input 140 may be implemented with a touch panel and placed on the front of the display 150 to form a touch screen. While examples of input 140 are mentioned herein, the input 140 is not limited thereto and may include hardware, software or combination thereof that enables communication between hardware device(s), software program(s), a user, etc.

The display 150 may display screens representing an image for guiding input of the user, an X-ray image, a camera image, and/or a state of the X-ray imaging apparatus 100.

An X-ray detector 200 may be implemented as a fixed type of X-ray detector fixed on a stand 20 or a table 10, or may detachably equipped in an install part 14, 24. Alternatively, the X-ray detector 200 may be implemented as a portable X-ray detector available at any place. The portable X-ray detector may further be classified into a wired type and a wireless type depending on the data transfer method or the power supplying method.

In the embodiment, a mode in which X-raying is performed with the X-ray detector 200 installed in an install part 14 of the imaging table 10 is called a table mode; a mode in which X-raying is performed with the X-ray detector 200 installed in an install part 24 of the imaging stand 20 is called a stand mode; a mode in which X-raying is performed with the X-ray detector 200 not installed in the install part 14, 24 but located behind an imaging portion of the subject is called a portable mode.

The X-ray detector 200 mounted on the install part 14, 24 may be moved automatically or manually. In the former case, the X-ray imaging apparatus 100 may further include a driver, such as a motor to provide power to move the install part 14, 24.

The X-ray detector 200 may or may not be included as an element of the X-ray imaging apparatus 100. In the latter case, the X-ray detector 200 may be registered in the X-ray imaging apparatus 100 by the user. Furthermore, in both cases, X-ray images obtained by the X-ray detector 200 detecting X-rays may be sent to the workstation 180.

A sub user interface 80 may be arranged on one side of the X-ray source 110 to provide information for the user and receive a command from the user, and may perform a part or all of the functions performed by the input 140 and the display 150 of the workstation 180.

In an embodiment, the X-ray imaging apparatus 100 may be implemented as tomosynthesis equipment, which takes images of the subject from different angles or views while moving the X-ray source 110, thereby obtaining tomograms or three-dimensional (3D) data of the subject.

Figure 2:
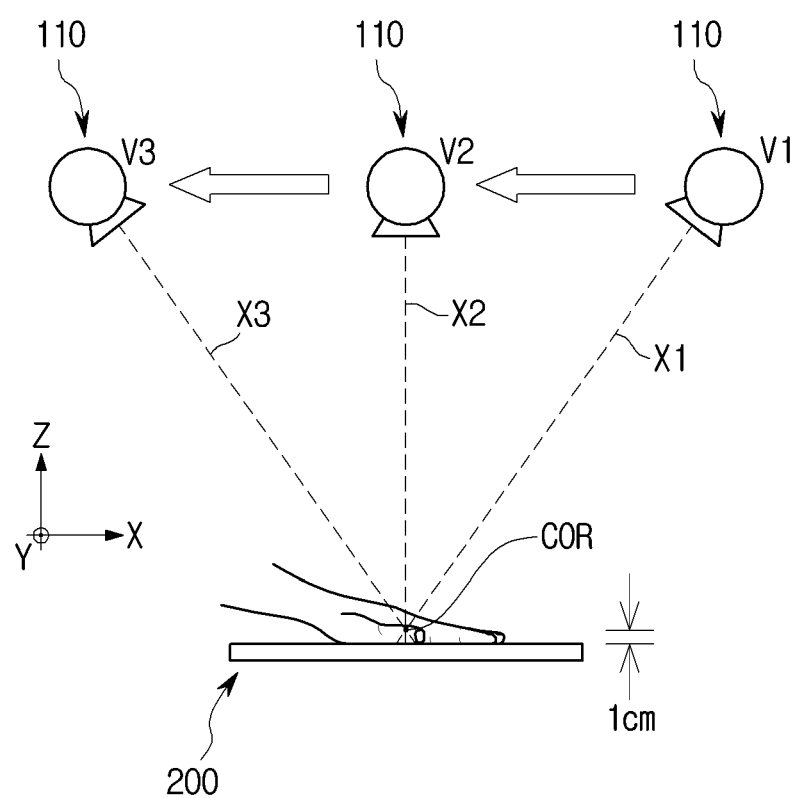
FIGS. 2 to 4 show the center of rotation of an X-ray source that varies by thickness of a subject and imaging protocol.
Figure 3:
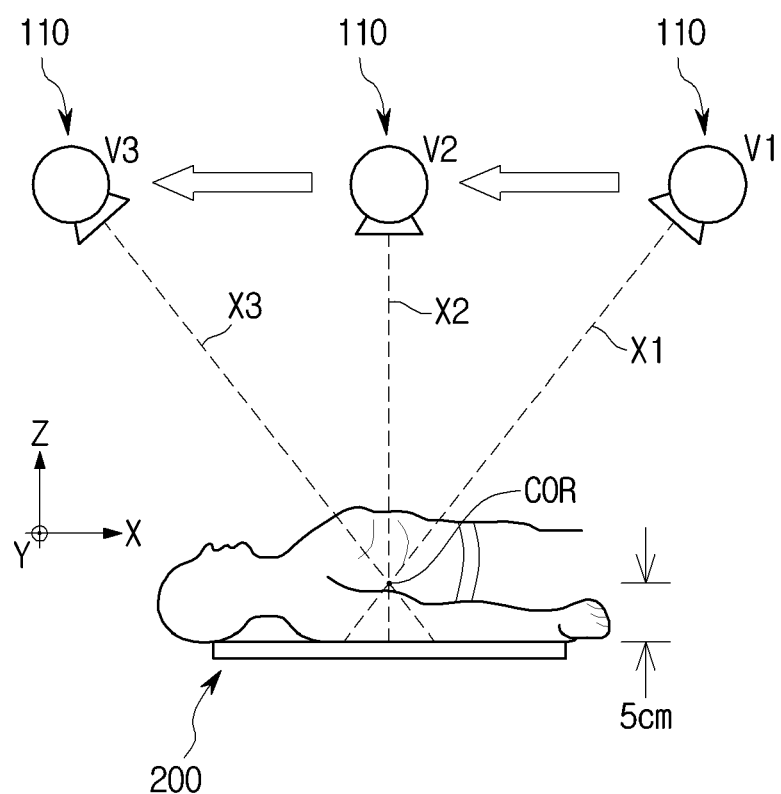
Figure 4:
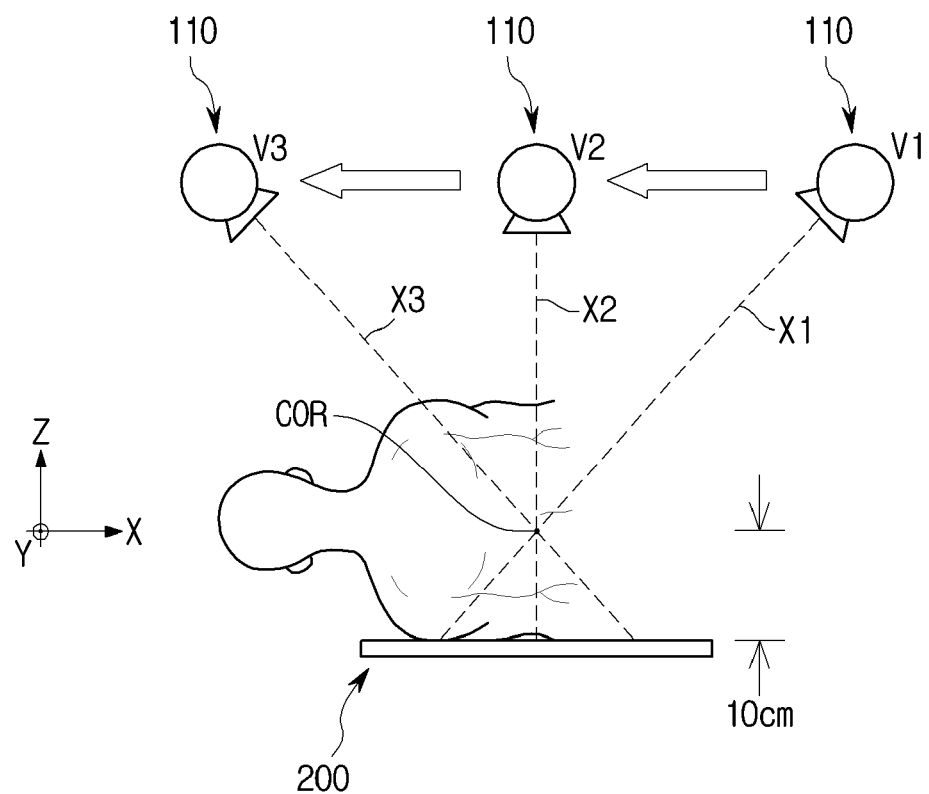

FIGS. 2 to 4 show the center of rotation of an X-ray source that varies by thickness of a subject and imaging protocol.

Referring to FIGS. 2 to 4, when a portion to be scanned (hereinafter, referred to as a scanning portion) of a subject is located on top of the X-ray detector 200, the X-ray source 110 may rotate around the scanning portion and irradiate X-rays X1, X2, and X3 thereto from a plurality of views V1, V2, and V3, thereby obtaining a plurality of projection images. In this regard, the rotation of the X-ray source 110 may be performed by linear motion along the guide rail 30 and by changing tilt angles or rotation angles using the rotary joint 60 which may include the first rotary joint 61 and the second rotary joint 62.

The center of rotation (COR) of the X-ray source 110 may be set to be the center of the scanning portion. Accordingly, the COR on the z-axis varies by thickness of the scanning portion. The x-, y-, and z-axes are relative to each other, and in this embodiment, a plane parallel to the plane of the X-ray detector 200 corresponds to the xy-plane and the z-axis corresponds to the incidence direction of an X-ray or the thickness direction of the subject.

In the case that the scanning portion corresponds to a hand as shown in FIG. 2 and in the case that the scanning portion corresponds to an abdominal region as shown in FIGS. 3 and 4, the COR of the X-ray source 110 may differ due to the difference in thickness between portions to be scanned (scanning portions).

Even for the same scanning portion, the COR of the X-ray source 110 may differ by imaging protocol. For example, as shown in FIGS. 3 and 4, even in the case of scanning the same abdominal region, the thickness of the subject with respect to the incidence direction of the X-ray may differ from the anterior posterior (AP) protocol according to which the subject is scanned from the front (FIG. 3) to the lateral protocol according to which the subject is scanned from the side (FIG. 4), so the COR of the X-ray source 110 may differ as well.

However, since the conventional X-ray imaging apparatus does not measure the thickness of a subject, the COR is set on the surface of the X-ray detector 200 or fixedly set in other different position, so that it has an error in the COR depending on the thickness of a scanning portion or a protocol type, causing degradation of the resolution of X-ray images in the depth direction.

In an embodiment of the present disclosure, to prevent the degradation of the resolution due to the error in COR, the X-ray imaging apparatus 100 measures thickness of a subject and determines the COR of the X-ray source 110 taking into account the thickness of the subject and a region of interest. Features and operations related to this will now be described in detail.

Figure 5:
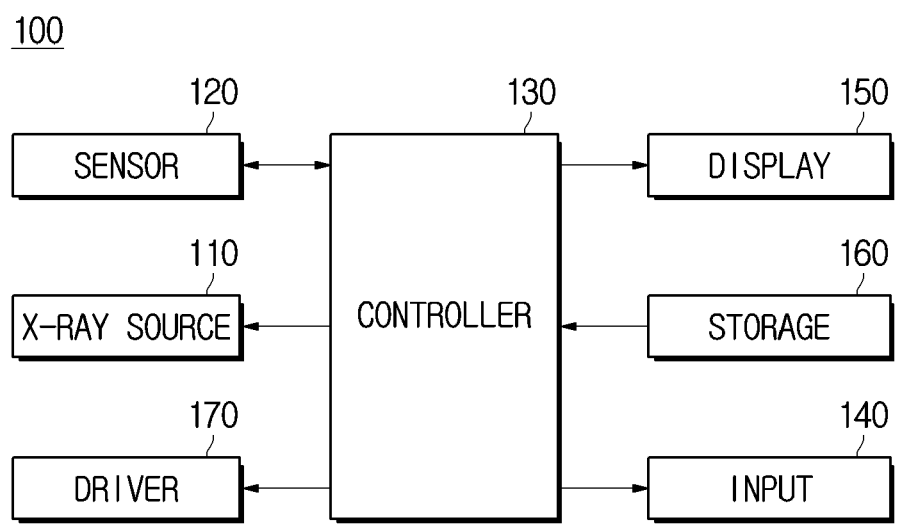
FIG. 5 is a control block diagram of an X-ray imaging apparatus, according to an embodiment of the present disclosure.

FIG. 5 is a control block diagram of an X-ray imaging apparatus, according to an embodiment of the present disclosure.

Referring to FIG. 5, the X-ray imaging apparatus 100 in accordance with an embodiment includes the X-ray source 110 for generating and irradiating X-rays onto a subject, a sensor 120 for obtaining a distance between the X-ray source 110 and the subject, a controller 130 for measuring thickness of the subject based on the output of the sensor 120 and determining the COR of the X-ray source 110 based on the thickness of the subject, a display 150 for displaying information regarding the thickness of the subject, an input 140 for receiving a designated region of interest from the user, a storage 160 for storing data required to calculate the thickness of the subject, such as a source to image distance (SID), which is a distance between the X-ray source 110 and the X-ray detector 200, and a driver 170 for moving the X-ray source 110 according to the determined COR.

The X-ray source 110 includes an X-ray tube for generating X-rays and a collimator for regulating an irradiation range of X-rays generated from the X-ray tube.

The sensor 120 may measure a source to object distance (SOD), which is a distance between the X-ray source 110 and the subject, or may obtain data required to measure the SOD. For example, the sensor 120 may include at least one of a camera, a stereo camera, a depth camera, a photo sensor, an ultrasonic sensor, and a laser sensor. The cameras and sensors are only by way of example, and the embodiment of the X-ray imaging apparatus 100 is not limited thereto.

The controller 130 may obtain thickness of a subject based on the SOD and SID and determine the COR of the X-ray source 110 based on the thickness of the subject. The COR determined based on the thickness of the subject corresponds to a center of rotation with respect to a direction of X-ray irradiation, i.e., a center of rotation on the z-axis. The COR on the xy-plane may be set to the center of the surface of the X-ray detector 200 or to other point than the center of the surface of the X-ray detector 200 according to where the region of interest is.

The controller 130 controls movement of the X-ray source 110 based on the determined COR. As described above, the X-ray source 110 may be moved linearly along the guide rail 30 installed on the ceiling and may be rotated in the fourth and fifth directions D4 and D5 according to the rotation of the rotary joint 61, 62. Accordingly, the controller 130 may send a control signal to the driver 170 to make the X-ray source 110 move linearly and rotate based on the determined COR, and the driver 170 may provide power for the X-ray source 110 to be moved linearly and rotated.

The driver 170 may include at least one motor and driving circuit to provide the power to the X-ray source 110.

Furthermore, the controller 130 may set an entire scanning angle and control the movement of the X-ray source 110 based on the entire scanning angle and the COR. The entire scanning angle indicates a range in which the X-ray source 110 is rotated while making linear motion from left to right or from right to left. Referring to FIG. 2, an angle formed by the X-ray X1 irradiated to the COR from the first view V1 and the X-ray X3 irradiated to the COR from the third view V3, which is the last view, may correspond to the entire scanning angle.

The controller 130 may also control a view interval. Turning back to FIG. 2, the view interval may be represented by an angle between neighboring views, i.e., an angle formed by X-rays irradiated to the COR from the neighboring views.

For example, the view interval may be set by taking into account a distance between the eyes of a human and an SOD. In this case, assuming that the distance between the eyes of a human is 6.5 cm and the SOD is about 60 cm, the view interval may be set to 6 degrees. Once the view interval is set, the number of views, i.e., the number of shooting times, is determined based on the entire scanning angle and the view interval.

For example, if the entire scanning angle is set to 84 degrees and the view interval is set to 6 degrees, the controller 130 may control the X-ray source 110 to irradiate X-rays at intervals of 6 degrees while rotating within a range of 84 degrees, thereby performing scanning from 15 views as many as a total of 15 times and thus obtaining 15 two-dimensional (2D) projection images.

Furthermore, the controller 130 may control X-ray irradiation conditions, X-ray irradiation timing, etc., and create an X-ray image used for diagnosis by processing data received from the X-ray detector 200.

The X-ray irradiation condition may be determined depending on the feature of the subject or the imaging protocol. The X-ray irradiation condition may include at least one of exposure parameters, such as a tube voltage (Kvp), a tube current (mA), exposure time (s), a filter type and thickness, a target material of anode, focal spot size, etc., and scatter parameters, such as a grid angle or center position, field of view (FOV), etc.

Relations between the feature of the subject or the imaging protocol and the X-ray irradiation condition may be stored in the storage 160 in advance.

The controller 130 may set up the X-ray irradiation condition using the thickness of the subject obtained based on the SOD.

The controller 130 may create a tomogram by reconstructing a plurality of 2D projection images obtained from different views. As a method for reco nstructing the 2D projection image, there may be an iterative method, a direct Fourier method, a filtered back projection method, or the like.

The controller 130 may also create three-dimensional (3D) volume data of the subject through 3D reconstruction of the volume of the subject. The 3D reconstruction is a method for restoring the volume of an object in 3D space comprised of voxels by using 2D images of the object. With the use of the 3D reconstruction method, the volume of the subject may be reconstructed from a plurality of tomograms.

The controller 130 may include a memory for storing a program for carrying out the aforementioned operations and the following operations, and a processor for executing the program. The controller 130 may include a single processor or multiple processors, and in the latter case, the multiple processors may be integrated in a single chip or may be physically separated.

In the case that the controller 130 includes the multiple processors and multiple memories, some of the multiple processors and memories may be included in the workstation 180, and some others in the sub user interface 80, the moving carriage 40, or other device. For example, the processor included in the workstation 180 may perform control, such as image processing to create a medical image, and the processor included in the sub user interface 80 or the moving carriage 40 may perform control over the movement of the X-ray source 110 or the X-ray detector 200.

The storage 160 may store information about patients, information about X-ray irradiation conditions, information about SIDs, information required to obtain an SOD, etc. The storage 160 may also store X-ray images per patient or study. The storage 160 may also store information about positional relations between a camera image and an X-ray image.

Figure 6:
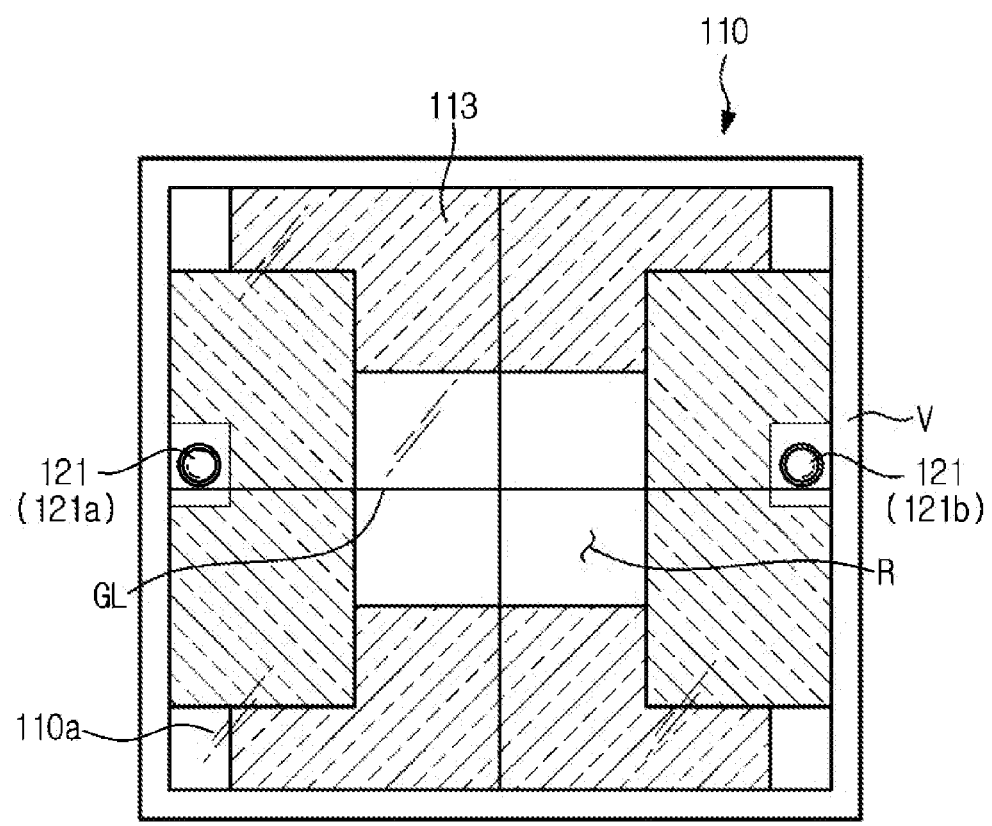
FIG. 6 is an external view illustrating a sensor in an X-ray imaging apparatus, according to an embodiment of the present disclosure.
Figure 7:
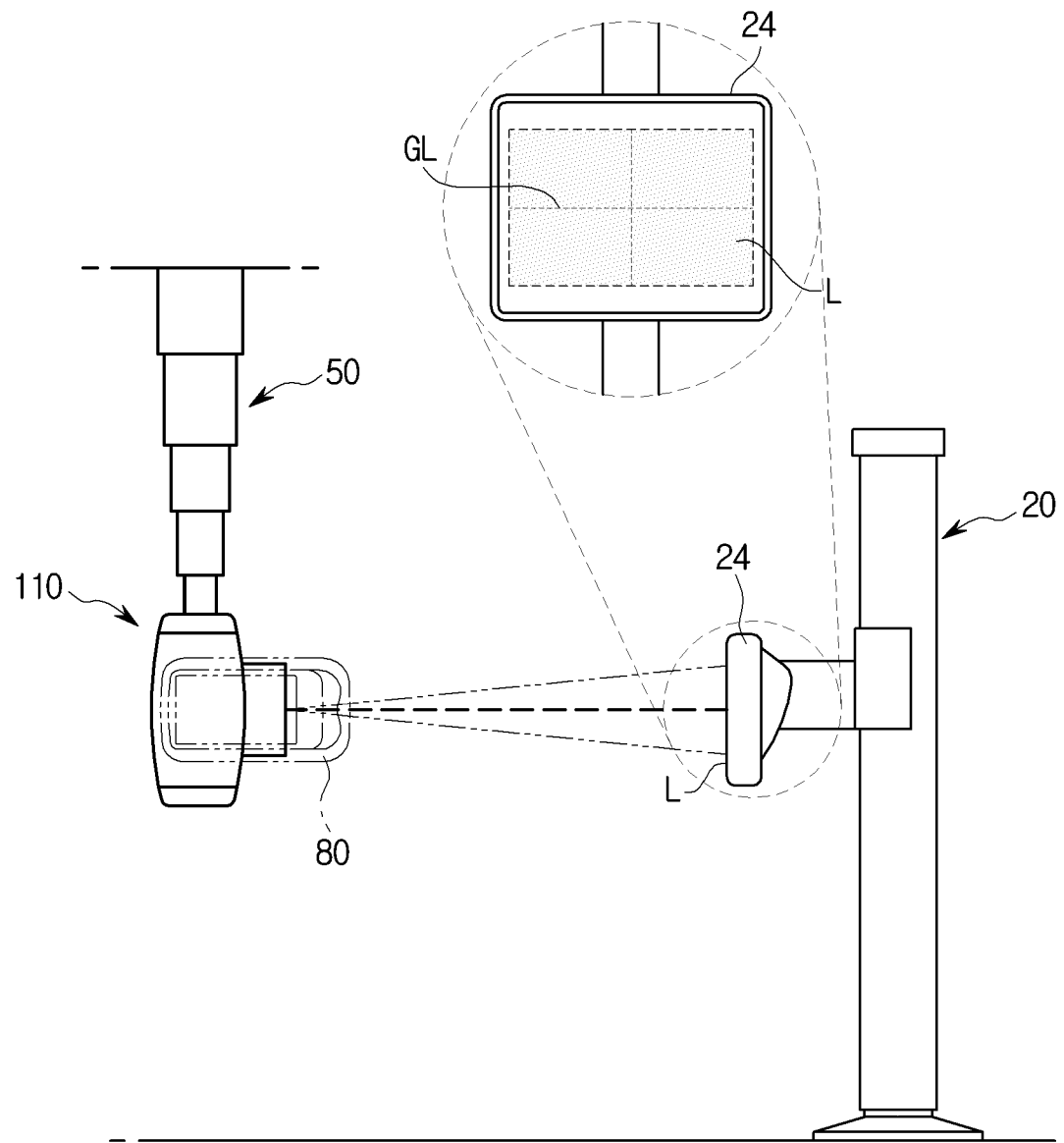
FIG. 7 shows an area of visible rays irradiated from an X-ray source.

FIG. 6 is an external view illustrating a detector in an X-ray imaging apparatus, according to an embodiment of the present disclosure, and FIG. 7 shows an area of visible rays irradiated from an X-ray source. FIG. 6 shows the X-ray source 110 viewed from a direction in which an X-ray is irradiated.

Referring to FIG. 6, the sensor 120 may include a stereo camera 121, and the stereo camera 121 may include a left-side camera 121a and a right-side camera 121b.

The stereo camera 121 may be placed in a position where a portion to be X-rayed (hereinafter, also called an X-raying portion) of the subject may be scanned. For example, it may be installed in the same direction in which the X-ray source 110 irradiates an X-ray.

To distinguish camera images from X-ray images, images captured by the camera will be referred to as camera images (including both images containing and not containing the subject).

Once the stereo camera 121 is installed in the X-ray source 110, an offset between an area appearing in the X-ray image and an area appearing in the camera image becomes small, so the camera image may be used in various usages in addition to obtaining the SOD.

For example, the left-side camera 121a may be provided on the left inside of a bezel V and the right-side camera 121b may be provided on the right inside of the bezel V. Where to place the stereo camera 121 may be suitably determined within a range that does not affect X-raying.

A housing 110a is formed in front of a collimator 113 and may be made of a material such as a transparent resin or glass to minimize its influence to an X-ray irradiated through a slot R.

The stereo camera 121 may be embedded inside the housing 110a of the X-ray source 110, as shown in FIG. 6, without being limited thereto. The stereo camera 121 may also be installed outside the X-ray source 110 or on the outside of the bezel V. There are no limitations on where to place the stereo camera 121 as long as the stereo camera 121 is able to take an image of the subject.

There may be a marker on the housing 110a to indicate the center of a collimation region. For example, a cross guide line GL may be marked on the housing 110a. Embodiments of the X-ray imaging apparatus 100 are not, however, limited thereto, and other shapes like a polygon, a circle, etc., than the cross shape may also be marked on the center of the collimation region as a marker.

As shown in FIG. 7, when a collimator lamp embedded in the X-ray source 110 irradiates a visible ray (VL) while the X-ray source 110 is directed to the install part 24, the visible ray VL may form a light irradiation area L on the install part 24 and the collimator guide line GL may also be marked or formed on the install part 24 due to the shadow of the guide line GL marked on the housing 110a. The light irradiation area L may correspond to an X-ray irradiation area adjusted by the collimator 113.

If the subject is located in front of the install part 24, the light irradiation area L and the guide line GL may be formed on the subject. The user may intuitively know of the location of the area to which X-rays are irradiated by observing the guide line GL formed on the install part 24 or the subject.

The light irradiation area L formed by the visible ray VL from the collimator lamp and the guide line GL may appear in camera images taken by the stereo camera 121. The controller 130 may obtain an SOD using the camera image with the guide line marked therein.

First, the controller 130 may obtain internal and external parameters of the camera by performing camera calibration. For example, the camera calibration may be performed using a chessboard image.

Once left-side and right-side camera images with the guide line GL marked thereon are obtained, stereo matching may be performed in which camera parameters obtained through the camera calibration are used to find corresponding locations in the left-side and right-side camera images and correct the geometrical location.

Figure 8:
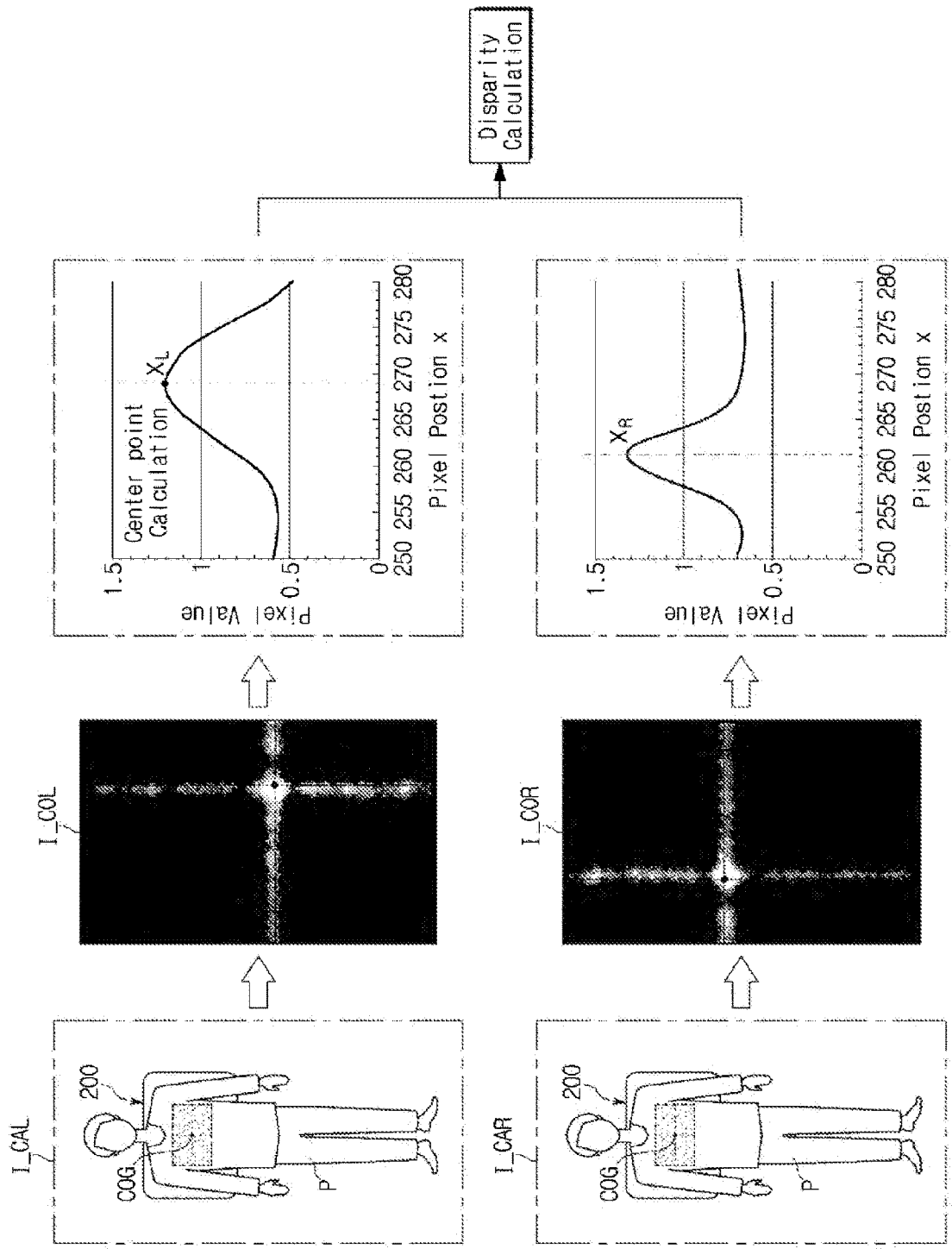
FIG. 8 schematically shows a process of obtaining coordinate information of a guide line using stereo camera images.

FIG. 8 schematically shows a process of obtaining coordinate information of a guide line using stereo camera images.

While the scanning portion of a subject P is positioned in front of the X-ray detector 200 and the X-ray source 110 is arranged at a position corresponding to the X-ray detector 200, the collimator lamp may irradiate the visible ray VL. Being located in front of the X-ray detector 200 even includes a case of being located in front of the X-ray detector 200 installed in the install part 14, 24.

As shown in FIG. 8, the guide line GL appears in the camera images I_CAL, I_CAR taken by the stereo camera 121, and a location of the center of the guide line GL (COG) may be assumed to be the center on the xy-plane of the X-raying portion.

The controller 130 may use template matching to obtain a correlated image I_COL to the guide line GL of the left-side camera image I_CAL and a correlated image I_COR to the guide line GL of the right-side camera image I_CAR.

Then, a location having the maximum pixel value in each correlated image may be determined to be the COG. Accordingly, using the maximum values of the respective correlated images, the points of the COGs $x_L$ and $x_R$ may be obtained from the left-side and right-side camera images, respectively.

By applying the two center points $x_L$ and $x_R$ to the following equation 1 based on triangulation, a distance Z between the stereo camera 121 and the COG may be obtained.

$$Z = B * f / (x_L - x_R) \quad (1)$$

The distance Z between the stereo camera 121 and the COG corresponds to the SOD. In the equation 1, B denotes a distance between the two cameras and f denotes a focal distance. These parameters may be obtained through camera calibration.

The controller 130 may obtain thickness of the subject using the SID and SOD. Specifically, a difference between the SID and the SOD corresponds to the thickness of the subject. The SID may be stored in the storage 160 in advance as a default value, or alternatively, may be calculated by the controller 130 based on the location of the X-ray source 110 moving along the guide rail 30 and a fixed location of the install part 14, 24.

Depending on the configuration of the stereo camera 121, the output of the stereo camera 121 may be stereo camera images or values of the distance Z. It is also possible that a processor is equipped in the stereo camera 121 to perform one of the aforementioned operations of the controller 130, which is related to obtaining the SOD.

After the thickness of the subject is obtained, the controller 130 may set the center of the thickness of the subject to the COR of the X-ray source 110 or provide the obtained information for the user to guide the user to designate a region of interest. This will be described later.

Figure 9:
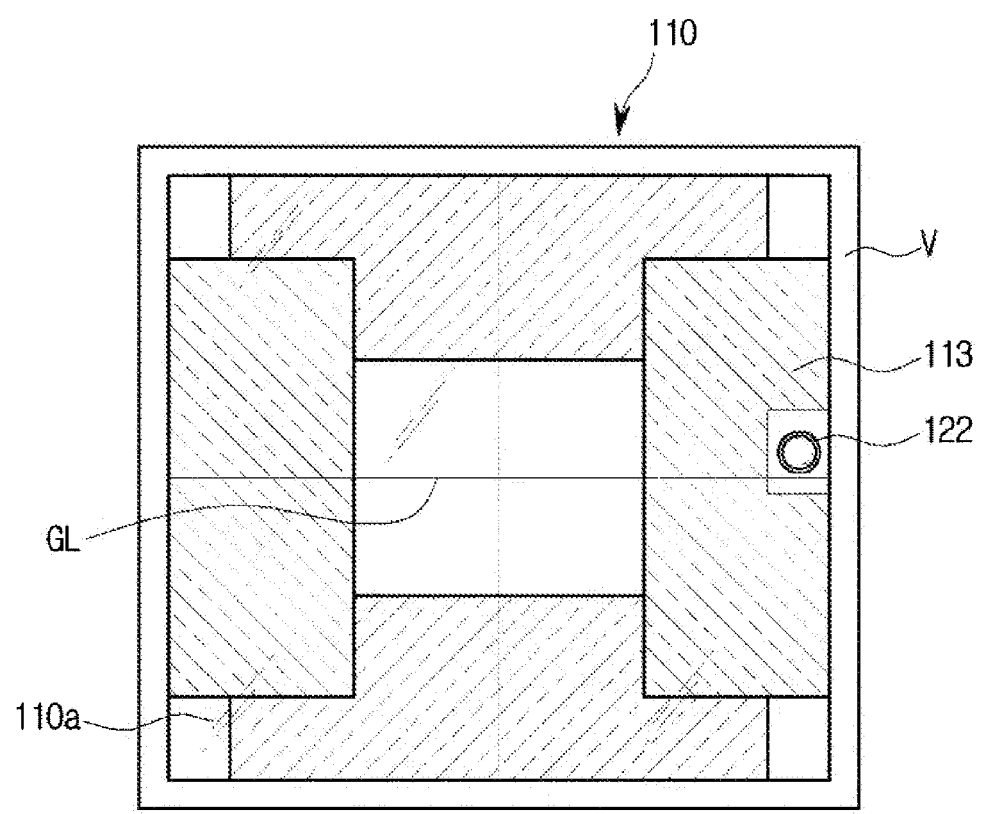
FIG. 9 is an external view illustrating a sensor in an X-ray imaging apparatus, according to another embodiment of the present disclosure.
Figure 10:
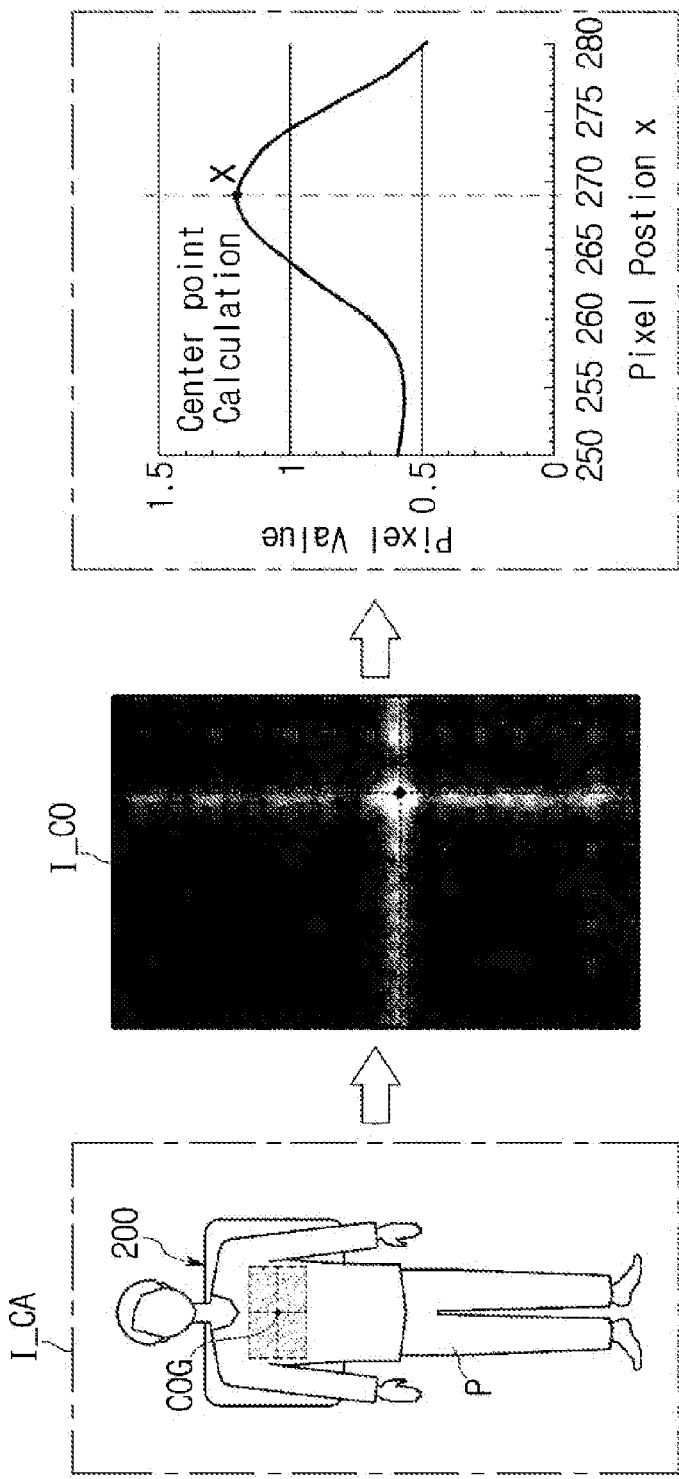
FIG. 10 schematically shows a process of obtaining coordinate information of a guide line using a camera image.
Figure 11:
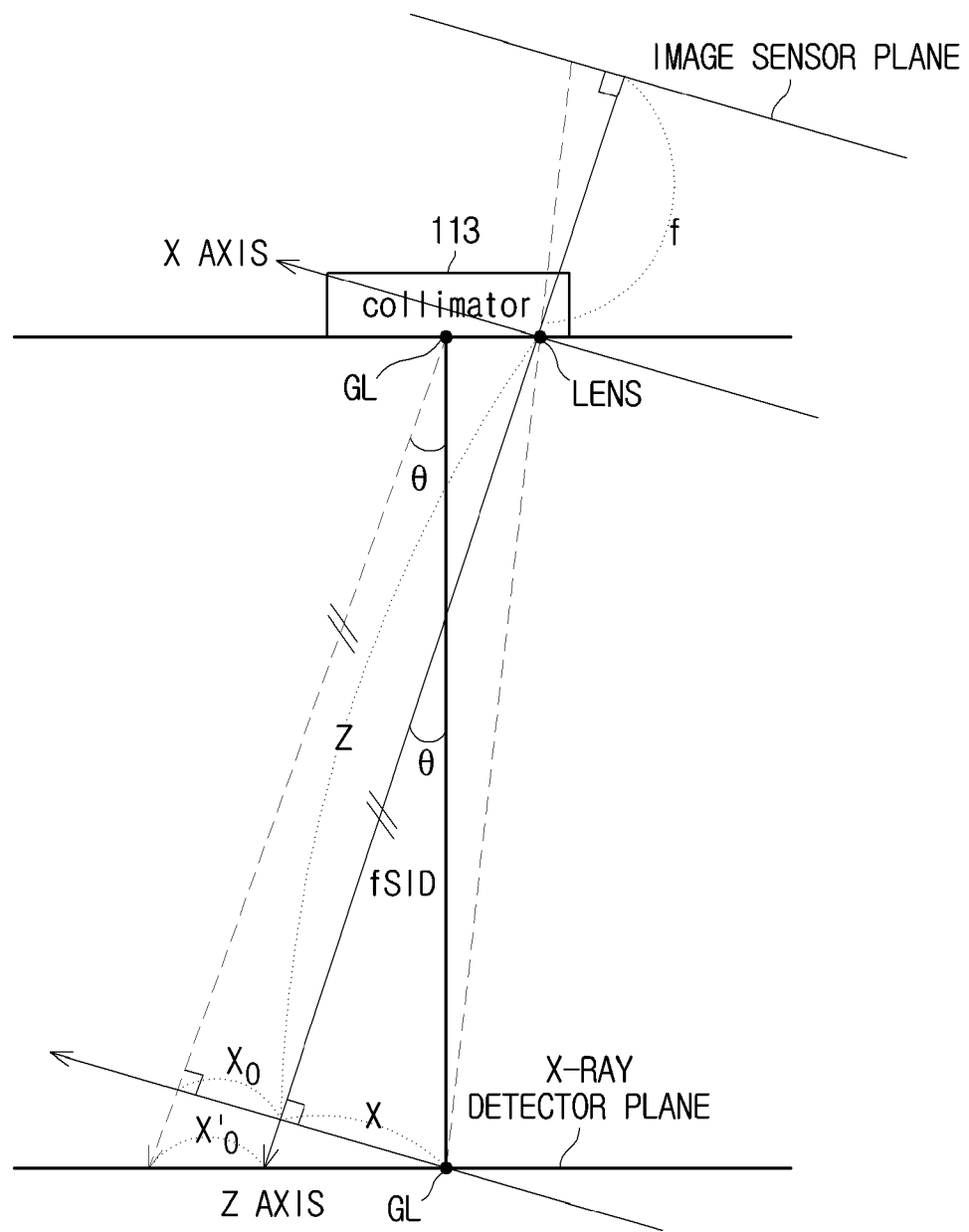
FIG. 11 shows relations between parameters used in a mathematical formula to obtain a source-object distance (SOD) using a single camera image.

FIG. 9 is an external view illustrating a detector in an X-ray imaging apparatus, according to an embodiment of the present disclosure, FIG. 10 schematically shows a process of obtaining coordinate information of a guide line using one camera image, and FIG. 11 shows relations between parameters used in a mathematical formula to obtain an SOD using a single camera image.

While the stereo camera 121 is used to obtain the SOD in the previous embodiment, a single camera 122 may be used to obtain the SOD in the following embodiment. The term 'single camera' is used to distinguish it from the stereo camera, and may refer to a normal charge-coupled device (CCD) camera or a complementary metal-oxide semiconductor (CMOS) camera.

Referring to FIG. 9, the single camera 122 may be placed at a position to take images of an X-raying portion of a subject or installed in the X-ray source 110, as well.

Although FIG. 9 shows that the single camera 122 is placed on the right inside of the bezel V, the single camera 122 may be placed on the left, top, or bottom inside of the bezel V or on the outside of the X-ray source 110 or bezel V.

Similar to what is described in the previous embodiment with the stereo camera 121, with a scanning portion of the subject P positioned in front of the X-ray detector 200 and the X-ray source 110 arranged at a position corresponding to the X-ray detector 200, the collimator lamp may irradiate the visible ray VL.

The guide line GL appears in the camera image I_CA taken by the single camera 122, and the COG may be assumed to be the center on the xy-plane of the X-raying portion.

The controller 130 may obtain internal and external parameters of the camera by performing camera calibration in advance. The controller 130 may also obtain a correlated image I_CO for the guide line GL of the camera image I_CA using template matching. By using the maximum value of the correlated image, the center point x of the guide line GL may be obtained from the camera image I_CA.

The storage 160 may formulate and store a relation between camera parameters, the center point of the guide line appearing in the camera image, and the SOD.

Referring to FIG. 11, if an axis parallel to the image sensor plane of the single camera 122 is defined as the x-axis and an axis perpendicular to the x-axis and passing through the lens is defined as the z-axis, the following equation 2 related to the SID may be derived using some parameters such as a distance between the image sensor plane and the lens (i.e., focal distance f).

$$fSID = \frac{1}{\tan\theta} \cdot \frac{fSID \cdot x}{f} + \frac{X_\theta}{\tan\theta \cdot \cos\theta} \quad (2)$$

where fSID denotes a distance between the surface of the collimator and the surface of the X-ray detector, θ denotes an angle formed by a straight line connecting the surface of the collimator and the surface of the X-ray detector and the x-axis, and x denotes x coordinates in the camera image. Relations between the respective parameters are shown in FIG. 11.

The following equation 3 may be derived from the equation 2.

$$SID = \frac{f \cdot \beta\_3d}{f - \alpha\_3d \cdot x} + \text{Offset} \quad (3)$$

where, α_3d=1/tan θ and β_3 d=X₀/cos θ tan θ. Furthermore, offset denotes a distance between the focal spot and the surface of the collimator.

In the procedure of deriving the above equations, the SID is used with no subject placed in front of the X-ray detector 200. However, once the subject is placed on the X-ray detector 200, the SID of equations 2 and 3 may be changed to the SOD. Accordingly, the controller 130 may obtain the SOD by applying the center point x of the guide line GL obtained from the camera image I_CA to the equation 3.

Depending on the configuration of the single camera 122, the procedure of calculating the SOD using a single camera image may be performed by the controller 130 or by the processor embedded in the single camera 122.

As another example of obtaining the SOD, it is possible for the sensor 120 to have a depth camera. The depth camera may acquire the depth information using a Time-of-Flight (TOF) technology. The TOF technology is to measure a distance by calculating time for an emitted signal to reflect off a subject and return.

In the case that the sensor 120 has the depth camera, it may include an infrared sensor and a color camera to acquire the depth information of a subject. For example, two color cameras may be installed on the front left and right sides of the X-ray source 110, and an infrared sensor may be installed between the two color cameras.

A depth image output by the depth camera may include the SOD. The controller 130 may extract the SOD from the depth image and obtain thickness of the subject using the SID and SOD.

It is also possible that the sensor 120 employs not only the aforementioned single camera, stereo camera, and/or depth camera but also various sensors used to measure a distance to an object, to obtain the SOD.

For example, a photo sensor including an emitter and a receptor may be employed. As described above in connection with the depth camera, a distance may be calculated by the TOF technology based on time for light irradiated from the emitter to reflect off the subject and return, by measuring an amount of light that reflects off the subject and returns, or by triangulation.

As a specific example, a distance may be obtained by irradiating infrared rays with the wavelength of about 900 nm or more by an infrared LED employed as the emitter and measuring an amount of infrared rays reflecting off the subject and returning. Since the amount of reflection is inversely proportional to the square of a distance, the less the amount of reflection, the farther the distance to the subject.

Alternatively, a position at which reflected rays are concentrated is measured by employing an infrared LED as the emitter to irradiate infrared rays, having the infrared rays reflecting off and returning concentrated through a lens and projecting the concentrated rays on a one-dimensional (1D) CCD sensor on the back. Since the distance between the emitter and the 1D CCD sensor is known in advance, a distance to the subject may be calculated based on the distance.

In another example, an ultrasonic sensor may be used, which includes a transmitter for transmitting ultrasounds and a receiver for receiving ultrasounds reflecting off the subject and returning. A distance to the subject may be measured using time for which the ultrasound reflects off and returns to the receiver and the traveling speed of the ultrasound.

In still another example, it is possible to use a laser sensor to calculate a distance to the subject by measuring a time delay of a phase.

The X-ray imaging apparatus 100 in accordance with an embodiment of the present disclosure may use various methods other than the aforementioned methods to measure the SOD.

In the above examples, the controller 130 knows of the information about the SID. In an embodiment, the X-ray imaging apparatus 100 has not only the stand mode and table mode, in which the X-ray detector 200 is mounted on the fixed install part 14, 24, but also a portable mode in which the X-ray detector 200 is used at an arbitrary position. Accordingly, an example of obtaining information about the SID when the X-ray imaging apparatus 100 performs X-raying in the portable mode will now be described.

Figure 12:
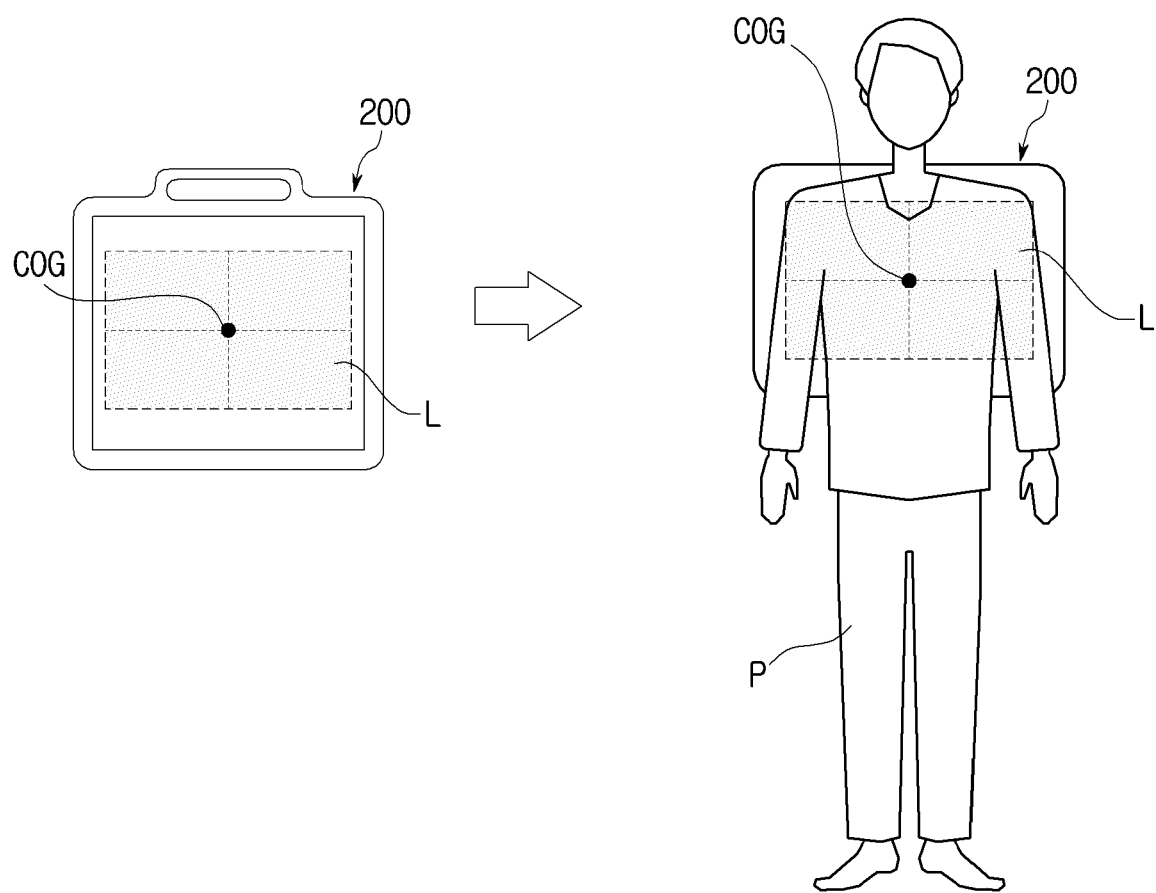
FIG. 12 shows an example of measuring a source-image distance (SID) and an SOD using camera images.

FIG. 12 shows an example of measuring an SID and an SOD using camera images.

In a case that the information about the SID is not stored in advance or that the controller 130 may not able to calculate the SID from the information stored in advance, the light irradiation area L and the guide line GL may be formed by irradiating visible rays onto the surface of the X-ray detector 200 before the subject P is placed on the front of the X-ray detector 200, and taken by the single camera 122 or the stereo camera 121 to calculate the COG and obtain the SID. This is the same as the operation of obtaining the SOD as described above with reference to FIGS. 6 to 10 except that the visible ray is irradiated directly to the X-ray detector 200 while the subject P is not placed on the X-ray detector 200.

After an image of the X-ray detector 200 with the light irradiation area L and the guide line GL formed on the surface is taken, the subject P may be placed on the X-ray detector 200 and the SOD may be obtained as described above.

Figure 13:
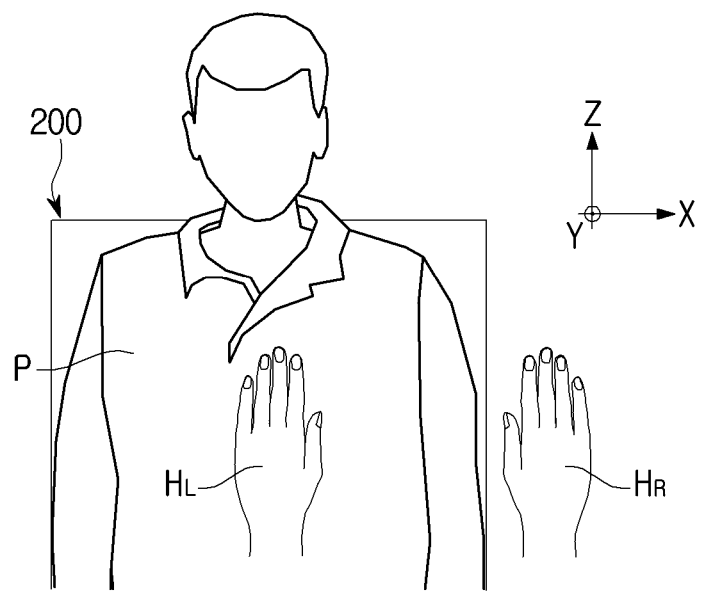
FIGS. 13 and 14 show an example of measuring both SID and SOD from one camera image.
Figure 14:
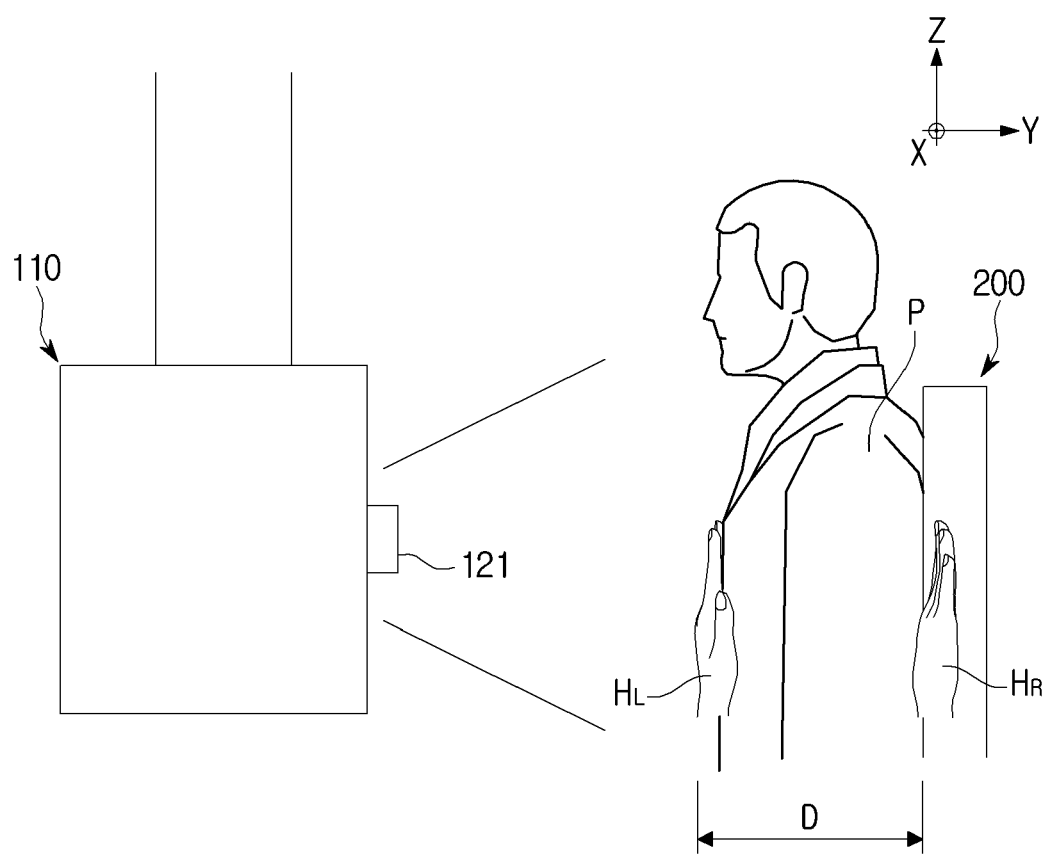

FIGS. 13 and 14 show an example of measuring both SID and SOD from one camera image.

In the previous examples, the guide line formed by the collimator lamp is used as an indicator to measure a distance to the subject in the camera image. Embodiments of the X-ray imaging apparatus 100 are not, however, limited thereto. For example, in the following embodiment, a plurality of indicators that represent thickness of the subject in one camera image may be detected, or the distance between the plurality of indicators may be used to obtain the thickness of the subject.

Specifically, one of the plurality of indicators may be located on the front face of an X-ray portion of the subject P and the other one may be located at a distance of the thickness of the X-raying portion away from the front face. The front face herein refers to a surface on which the X-ray is incident. Accordingly, the controller 130 may calculate the thickness of the subject P based on the distance between the plurality of indicators.

For example, the plurality of indicators may include both hands of the user. The user may put one hand on the front face of the X-raying portion of the subject while putting the other hand at a distance of the thickness of the X-raying portion away from the front face.

Referring to FIGS. 13 and 14, the user places one hand $H_L$ in front of the X-raying portion of the subject P while placing the other hand $H_R$ at the same point as the X-ray detector 200 on the Y-axis. For example, the distance between the hand HL placed in front of the X-raying portion and the X-ray detector 200 is equal to the distance between the hand $H_L$ and the other hand $H_R$. Accordingly, the distance on the Y-axis between the both hands $H_L$, $H_R$ of the user may be assumed to be equal to or almost similar to the thickness D of the X-raying portion of the subject P.

In this regard, to ensure that the both hands $H_L$, $H_R$ of the user appear in the camera image, they should not be hidden by the subject P or the X-ray detector 200.

In the embodiment, the sensor 120 may include the single camera, the stereo camera, or the depth camera, and the depth information of the subject may be obtained from the camera image taken by the sensor 120.

The controller 130 may use an object recognition algorithm to recognize each of the both hands $H_L$, $H_R$ appearing in the camera image and calculate the depth of either hand $H_L$, $H_R$.

The controller 130 may obtain the thickness D of the X-raying portion from the difference in thickness between the hand $H_L$ placed in front of the X-raying portion and the hand $H_R$ placed in the back of the X-raying portion.

In a case that the sensor 120 employs a distance measurement sensor, such as a photo sensor, an ultrasonic sensor, etc., a distance to the X-ray detector 200 may further be measured separately to obtain the SID.

Various methods for measuring thickness of a subject has thus far been described. Operation of setting the COR of the X-ray source 110 based on the thickness of a subject will now be described.

Figure 15:
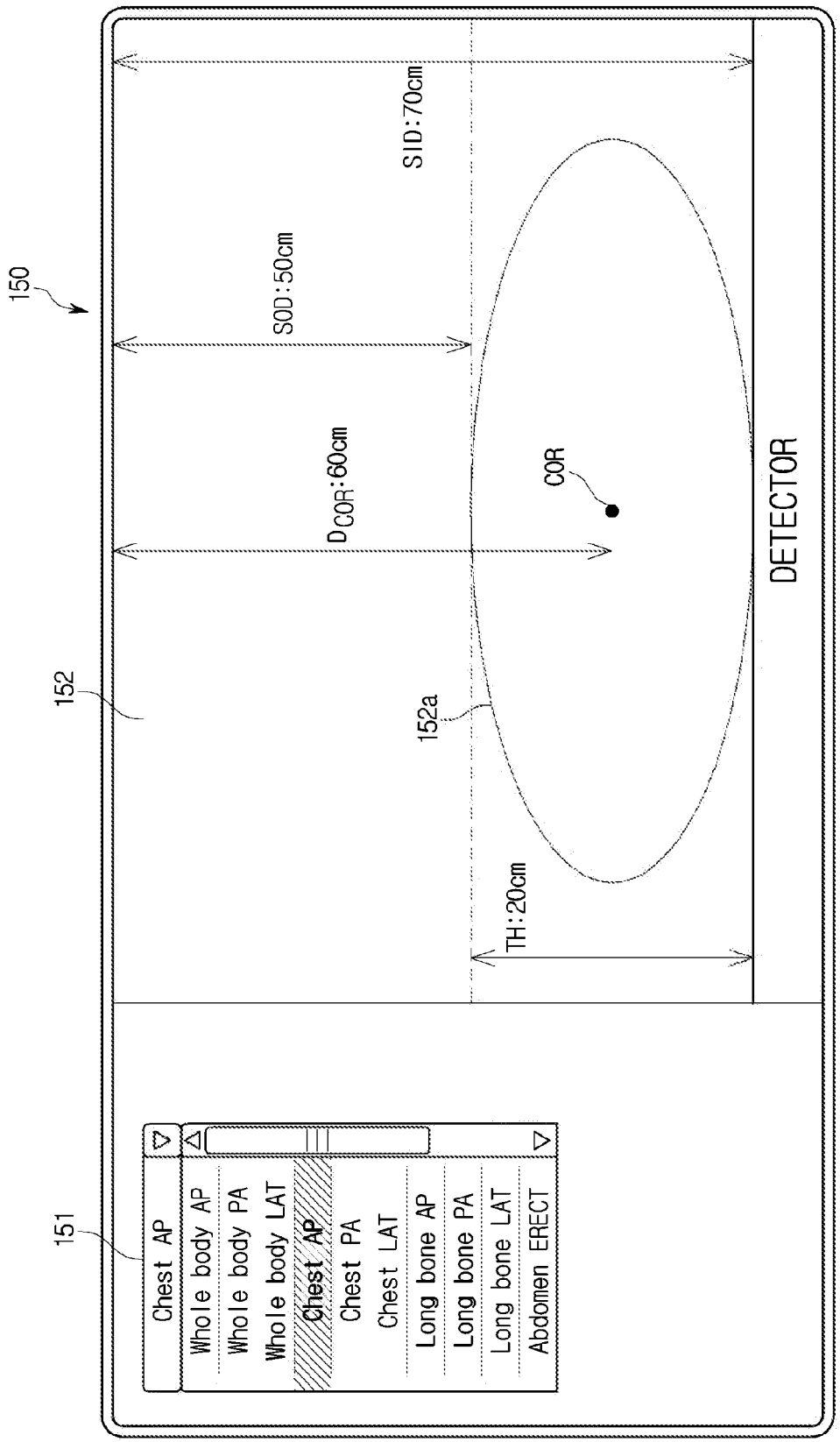
FIG. 15 shows how an X-ray imaging apparatus displays information about the center of rotation, according to an embodiment of the present disclosure.

FIG. 15 shows how an X-ray imaging apparatus displays information about the COR, according to an embodiment of the present disclosure.

Referring to FIG. 15, the display 150 may display a protocol list for the user to select an imaging protocol. The imaging protocol may be determined based on the X-raying portion, the posture of the subject, etc., and may include, for example, the whole body Anterior-Posterior (AP) to take an image of the entire body of the subject with its back to the X-ray detector, the whole body Posterior-Anterior (PA) to take an image of the entire body of the subject facing the X-ray detector, the whole body LAT to take an image of the entire body of the subject with its side to the X-ray detector. Even for the chest, there may be imaging protocols for capturing images in the AP, PA, LAT methods, and for long bones such as legs, there may be imaging protocols for capturing images in the AP, PA, LAT methods. However, the imaging protocols are only examples to be applied for the X-ray imaging apparatus 100, and other imaging protocols than the above examples may also be used.

Once an imaging protocol is selected, the controller 130 may automatically set an X-ray irradiation condition based on the thickness of the subject and the selected imaging protocol. Information about the X-ray irradiation condition based on the thickness of the subject and the imaging protocol may be stored in the storage 160 in advance. It is also possible for the user to change the automatically set X-ray irradiation condition.

The display 150 may provide information about the COR of the X-ray source 110 for the user or display a guide screen 152 to guide designation of a region of interest.

For example, a graphical object 152a corresponding to the subject may be displayed on the guide screen 152. The graphical object 152a may be a model that schematically represents the figure corresponding to the selected protocol, or may be a simplified diagram having a certain volume as shown in FIG. 15. In either case, the graphical object 152a may be displayed to have thickness proportional to the thickness of the subject obtained by the controller 130.

Furthermore, pieces of information obtained according to the previous embodiments may also be displayed with respect to the graphical object 152a. Information about a point of the COR may be displayed, and a distance from the X-ray source 110 to the X-ray detector 200 (SID), a distance from the X-ray source 110 to the subject (SOD), thickness of the subject (TH), and a distance from the X-ray source to the COR ($D_{COR}$) may be displayed in numerical values. In this embodiment, the center of the thickness of the subject (TH), i.e., the center of the subject in the direction of its thickness, is set as the COR.

Figure 16:
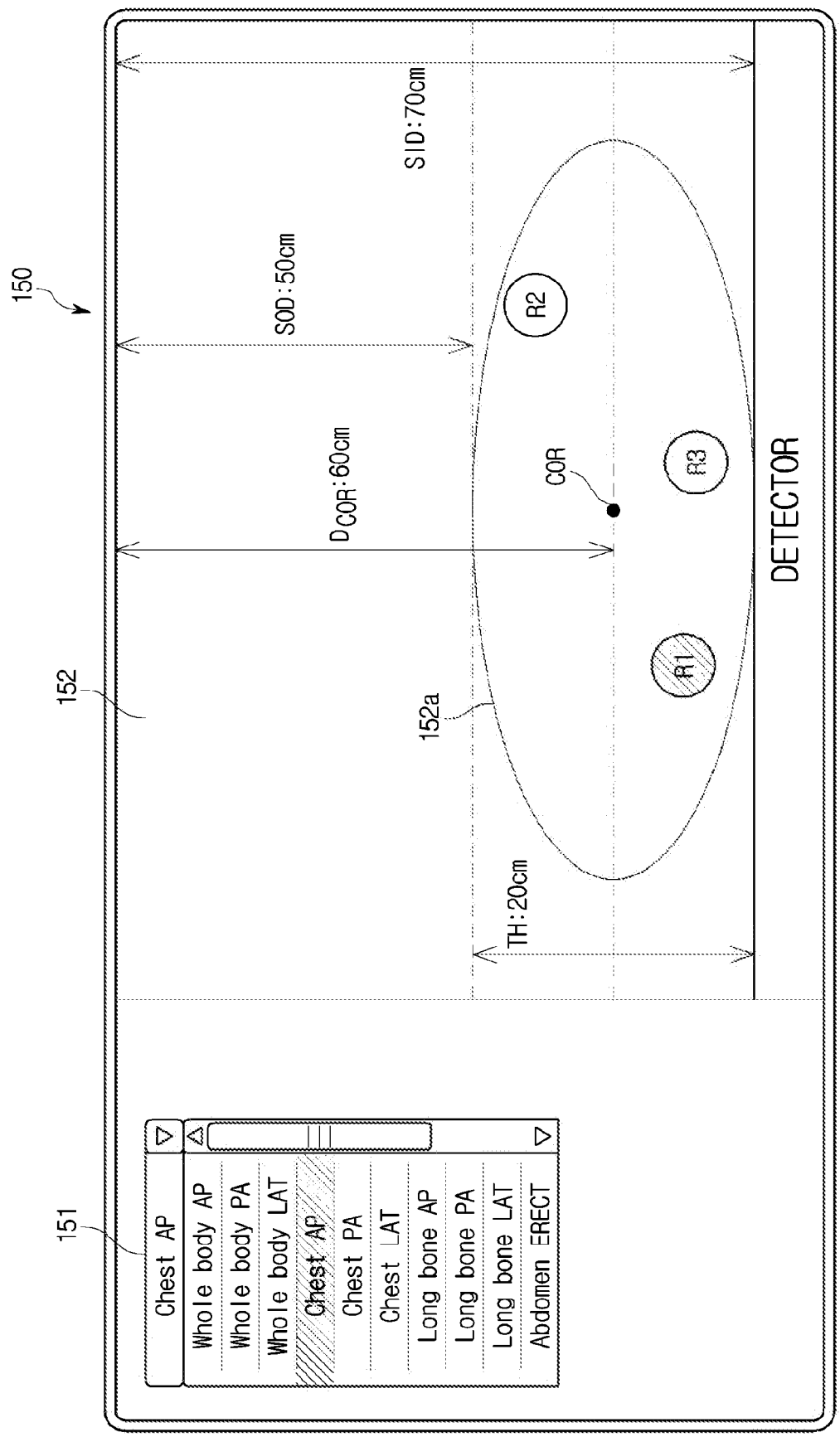
FIGS. 16 and 17 show how a user is able to designate a region of interest on a guide screen.
Figure 17:
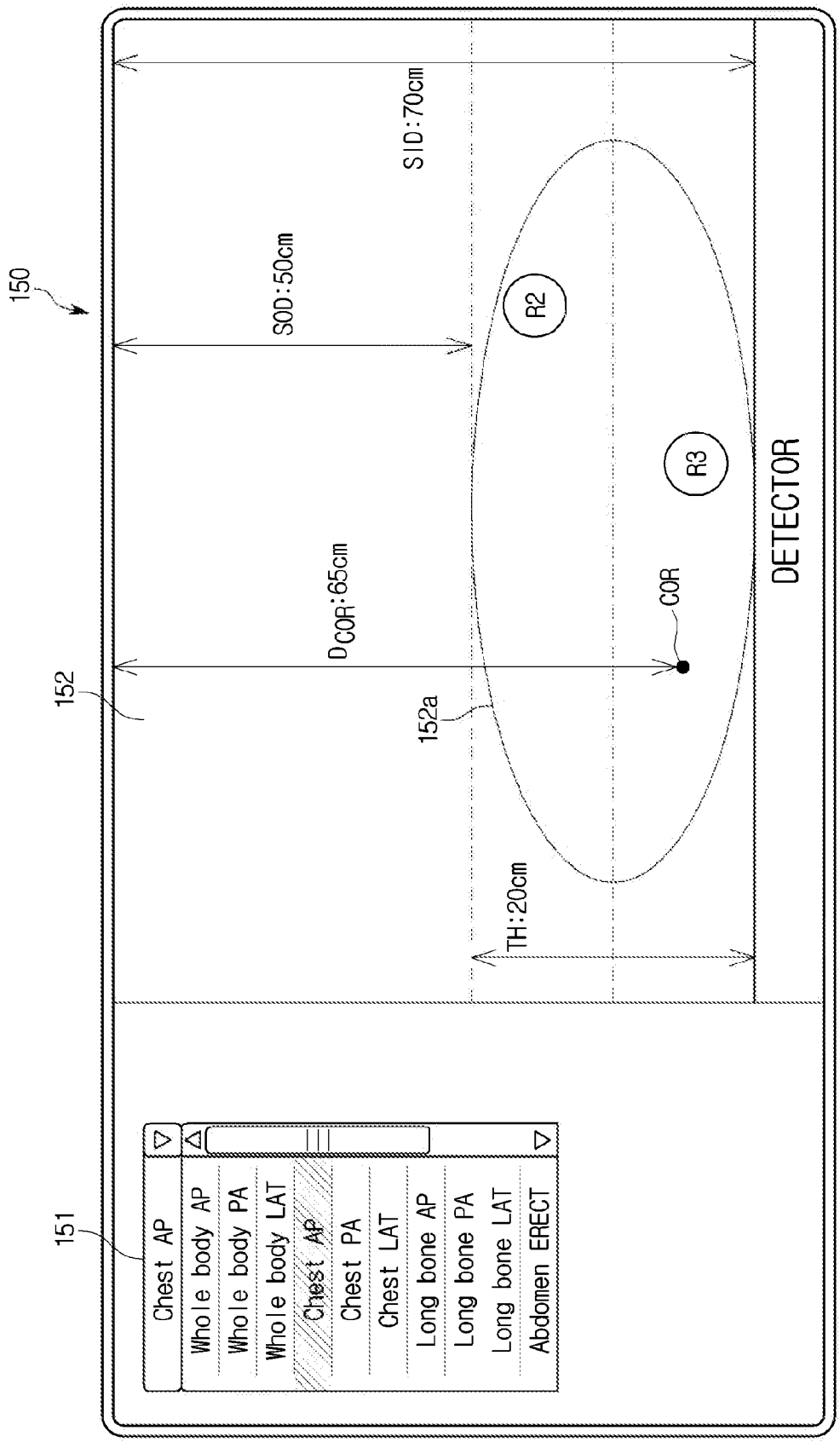

FIGS. 16 and 17 show how a user is able to designate a region of interest on a guide screen.

The user may have a region of interest even within the X-raying portion to observe with interest. Accordingly, as shown in FIG. 16, candidates of the region of interest R1, R2, and R3 may be displayed within the graphical object 152a that represents the subject, and the user may designate one of them.

If the input 140 includes a mouse or a keyboard, the user may select one of the candidates of the region of interest by moving a pointing tool like a cursor on the guide screen 152, and if a touch screen is implemented by the input 140 and the display 150, the user may touch and select a candidate of the region of interest.

Alternatively, it is possible for the user to designate a region of interest by selecting an arbitrary area within the graphical object 152a with no candidate of the region of interest displayed separately.

When the user designates a region of interest, the controller 130 may reset the COR of the X-ray source 110 based on the region of interest designated by the user. For this, the controller 130 may match respective positions within the graphical object 152a to positions in the actual subject and store them. For example, relations between positions on the graphical object 152a and thicknesses of the subject may be stored.

When the region of interest is designated, the controller 130 may determine a position of the region of interest in the direction of thickness based on a relation between the position of the region of interest designated on the graphical object 152a and the thickness of the subject, and set the position in the direction of thickness as the COR.

Furthermore, the controller 130 may recalculate a distance to the COR ($D_{COR}$) based on the changed COR and the display 150 may reflect and display the recalculated information.

As shown in FIG. 17, the display 150 may display the new COR on the guide screen 152 and update the distance from the X-ray source 110 to the COR ($D_{COR}$).

If the designation of a region of interest changes not only the position of the COR on the z-axis but also the position of the COR on the xy-plane, the controller 130 may control movement of the X-ray source 110 by reflecting the change.

Figure 18:
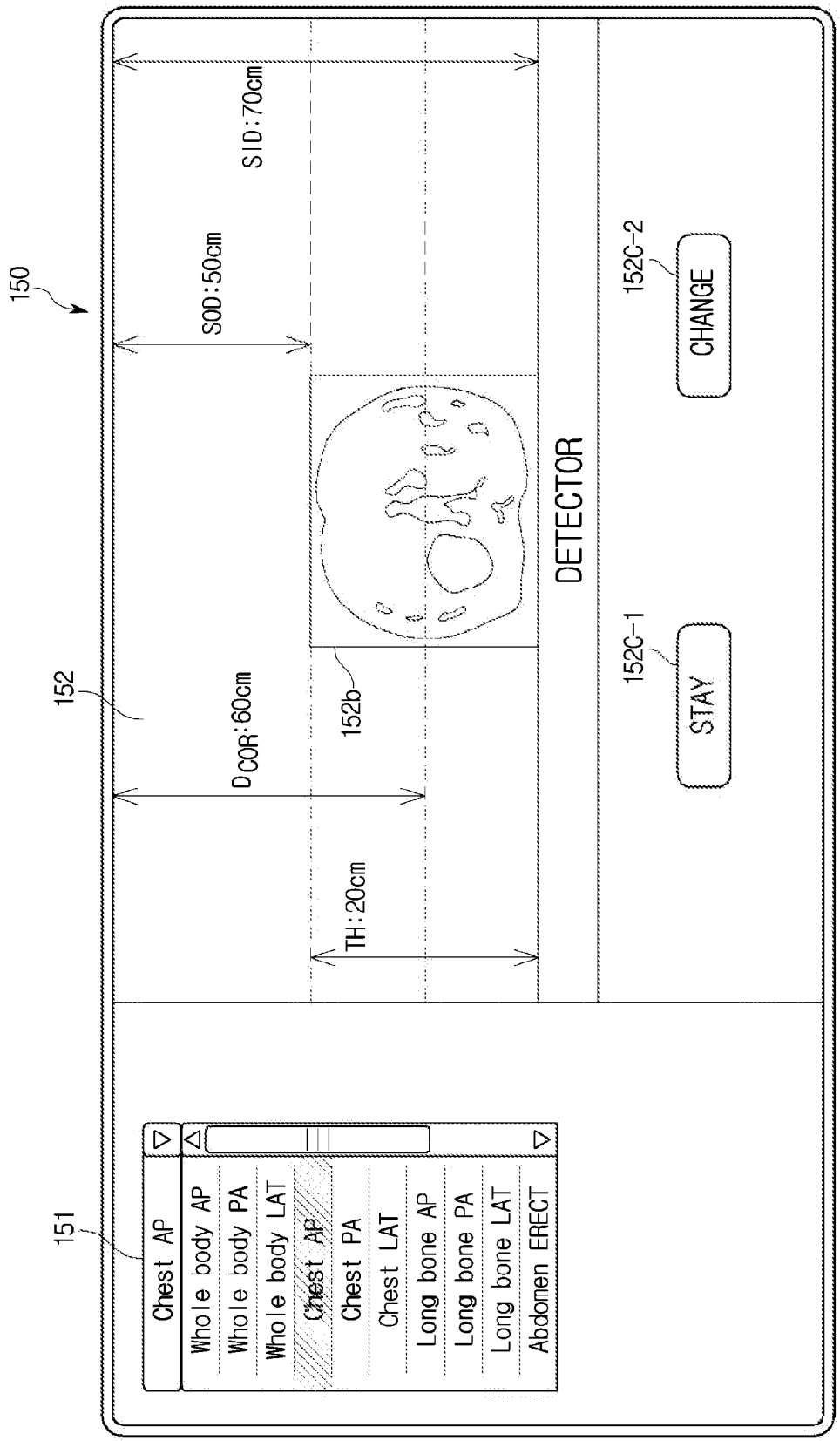
FIGS. 18 and 19 show an example of providing information using a previously captured X-ray image.
Figure 19:
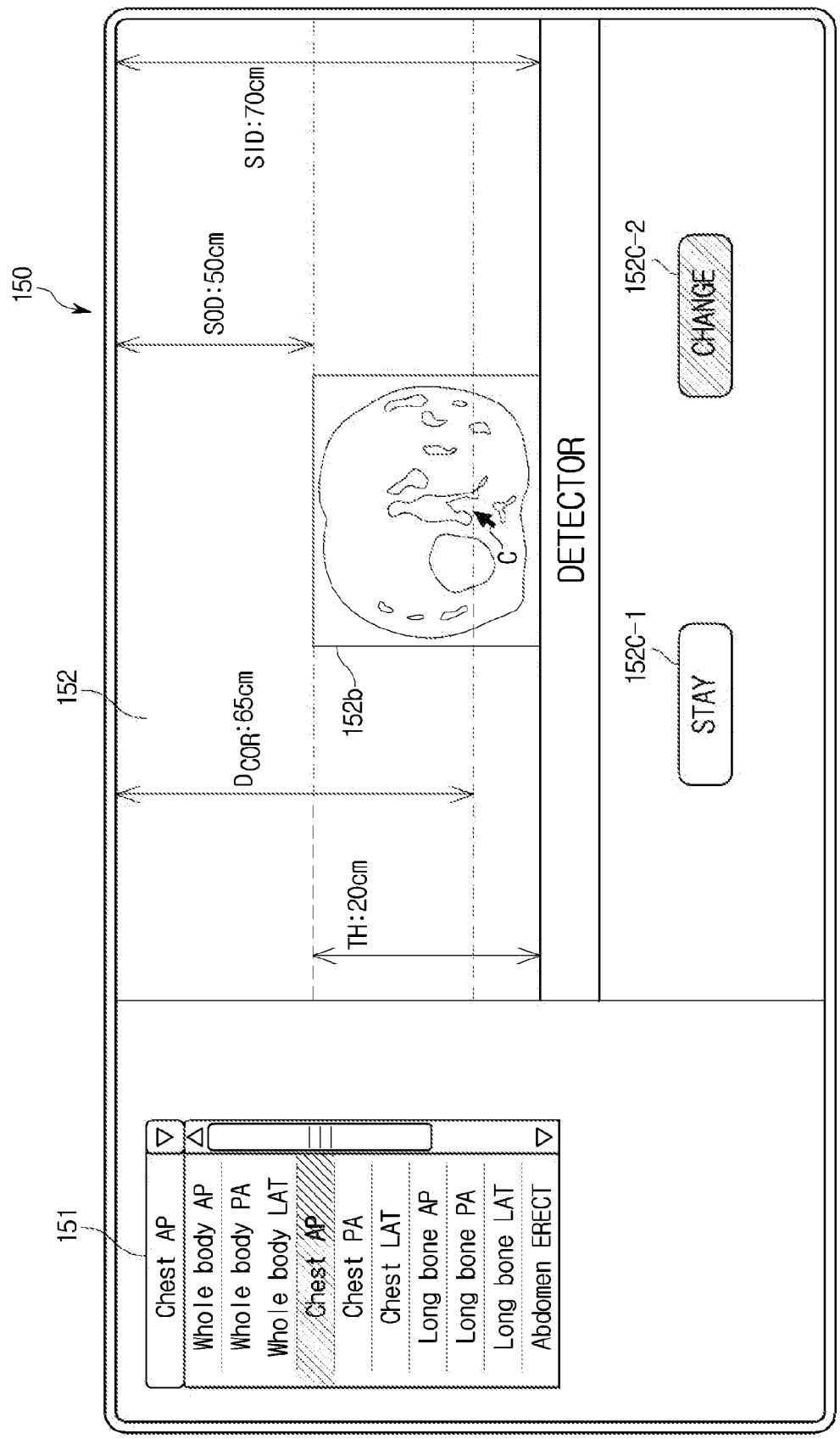

FIGS. 18 and 19 show an example of providing information using a previously captured X-ray image.

If there exists a previously captured X-ray image for the same patient, the graphic object may include the previous X-ray image. In this case, the display 150 may display a previous X-ray image 152b, as shown in FIG. 18. The previous X-ray image 152b may be a tomogram taken with the same protocol for the same patient.

For example, if a follow-up test is to be performed or if retaking is to be performed because a lesion suspicious area is found, the previous X-ray image for the same patient may have been stored in the storage 160.

Since the previous X-ray image 152b, which is a tomogram, includes information about thickness of the subject, the display 150 may display the thickness of the subject (TH) based on the previous X-ray image 152b and along with this, the display 150 may display the distance from the X-ray source 110 to the COR ($D_{COR}$), SID, and SOD.

With the presence of the previous X-ray image 152b, it is also possible to omit the aforementioned process of obtaining the thickness of the subject and to have the controller 130 measure the thickness of the subject appearing in the previous X-ray image 152b. In this case, time required to prepare for X-raying may be shortened and material costs may be saved by omitting extra equipment such as a camera or a sensor.

The user may apply the distance to COR ($D_{COR}$) displayed on the guide screen 152 as it is or may change the distance. For example, in the case of applying the displayed distance to COR ($D_{COR}$) as it is, a stay button 152c-1 may be selected, and in the case of changing the distance to COR ($D_{COR}$) as shown in FIG. 19, a region of interest or an area to be set to the COR is designated in the previous X-ray image 152b and a change button 152c-2 may be selected.

If the input 140 includes a mouse or a keyboard, the user may designate a region of interest by moving a pointing tool like a cursor on the previous X-ray image 152b, and if a touch screen is implemented by the input 140 and the display 150, a region of interest may be touched.

When the user designates a region of interest, the controller 130 may reset the COR of the X-ray source 110 to be the designated region of interest. Furthermore, the controller 130 may recalculate the distance to the COR ($D_{COR}$) based on the changed COR and the display 150 may reflect the recalculated information.

The display 150 may display the new COR on the guide screen 152 and update the distance from the X-ray source 110 to the COR (DCOR).

If the designation of a region of interest changes not only the position of the COR on the z-axis but also the position of the COR on the xy-plane, the controller 130 may control movement of the X-ray source 110 by reflecting the change.

Once the COR is set, the controller 130 may perform X-raying while linearly moving and rotating the X-ray source 110 based on the set COR, and reconstruct 2D projection images obtained by the X-raying to obtain a tomogram or 3D volume data.

A control method of an X-ray imaging apparatus in accordance with an embodiment of the present disclosure will now be described. The control method of an X-ray imaging apparatus may use the X-ray imaging apparatus 100 in accordance with the aforementioned embodiments. Even without being particularly mentioned, embodiments of the X-ray imaging apparatus 100 described in connection with FIGS. 1 to 19 may be equally applied to the control method of the X-ray imaging apparatus 100.

Figure 20:
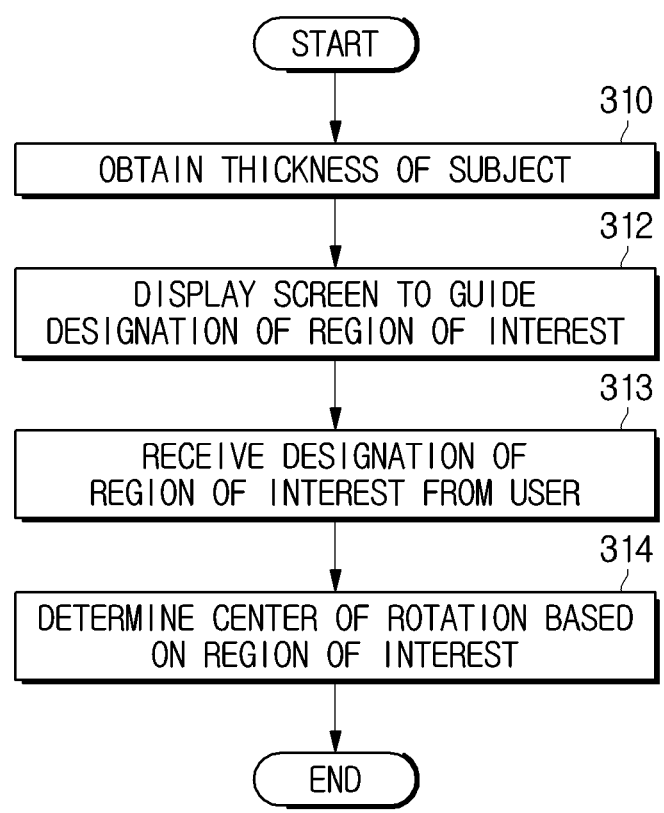
FIG. 20 is a flowchart of a control method of an X-ray imaging apparatus, according to an embodiment of the present disclosure.

FIG. 20 is a flowchart of a control method of an X-ray imaging apparatus, according to an embodiment of the present disclosure.

Referring to FIG. 20, thickness of a subject is obtained, in 310. The thickness of the subject may be obtained using a stereo camera, a single camera, a depth camera, a sensor for measuring a distance, etc. How to obtain the thickness of a subject will be described later in detail.

A screen is displayed to guide designation of a region of interest, in 312. For example, a graphical object 152a corresponding to a selected protocol may be displayed on the guide screen 152. Furthermore, pieces of information regarding the COR may also be displayed with respect to the graphical object 152a. A distance from the X-ray source 110 to the X-ray detector 200 (SID), a distance from the X-ray source 110 to the subject (SOD), thickness of the subject (TH), and a distance from the X-ray source to the COR ($D_{COR}$) may be displayed in numerical values. For example, the center of the thickness of the subject (TH) may be a default position of the COR.

Designation of a region of interest is received from the user, in 313. For example, candidates of the region of interest R1, R2, and R3 may be displayed within the graphical object 152a that represents the subject, and the input 140 may receive designation of one of them from the user. Alternatively, it is possible for the user to designate a region of interest by selecting an arbitrary area within the graphical object 152a with no candidate of the region of interest displayed separately.

A COR is determined based on the region of interest, in 314. When the user designates a region of interest, the controller 130 may reset the COR of the X-ray source 110 to be the designated region of interest. Furthermore, the controller 130 may recalculate a distance to the COR ($D_{COR}$) based on the changed COR and the display 150 may reflect the recalculated information.

The display 150 may display the new COR on the guide screen 152 and update the distance from the X-ray source 110 to the COR (DCOR).

Once the COR is set, the controller 130 may perform X-raying while linearly moving and rotating the X-ray source 110 based on the set COR, and reconstruct 2D projection images obtained by the X-raying to obtain a tomogram or 3D volume data.

Figure 21:
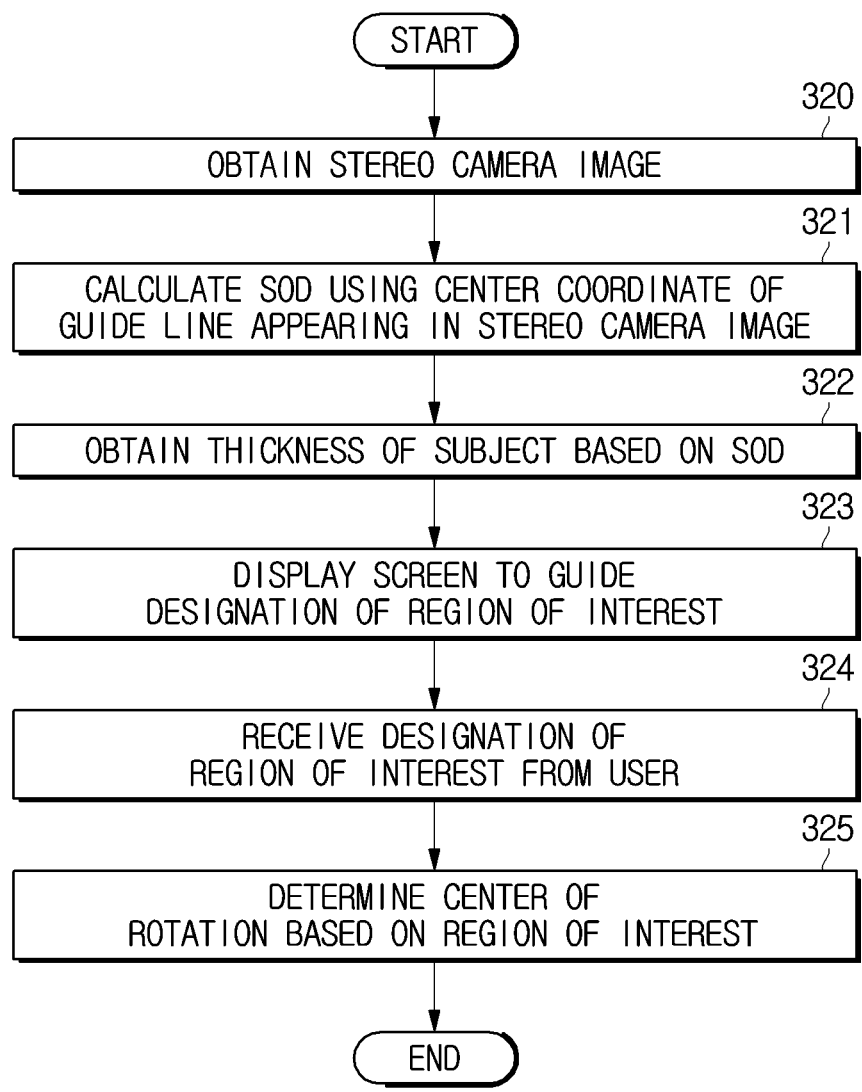
FIG. 21 is a flowchart of an instance of obtaining an SOD using a stereo camera in a control method of an X-ray imaging apparatus, according to an embodiment of the present disclosure.

FIG. 21 is a flowchart of an instance of obtaining an SOD using a stereo camera in a control method of an X-ray imaging apparatus, according to an embodiment of the present disclosure.

Referring to FIG. 21, stereo camera images are obtained, in 320. Again, the stereo camera 121 may include the left-side camera 121a and the right-side camera 121b, and the collimator guide line GL marked or formed on the surface of the subject P may appear in each of the left and right camera images.

An SOD is calculated using center coordinates of the guide line appearing in the stereo camera image, in 321. Stereo matching is performed to find corresponding locations in the left and right camera images based on camera parameters obtained through camera calibration. A correlated image I_COL to the guide line GL of the left-side camera image I_CAL and a correlated image I_COR to the guide line GL of the right-side camera image I_CAR may be obtained through template matching.

A location having the maximum pixel value in each correlated image may be determined to be the center of guideline COG. Accordingly, using the maximum values of the respective correlated images, the positions of the COGs $x_L$ and $x_R$ may be obtained from the left-side and right-side camera images, respectively. An SOD may be calculated by applying the obtained two center positions ($x_L$, $x_R$) in the triangulation method.

In the meantime, the process of calculating the SOD using the stereo camera images may be performed by the controller 130 or by the stereo camera 121.

Thickness of the subject is obtained based on the SOD, in 322. The controller 130 may obtain the thickness of the subject using the SID and SOD. Specifically, a difference between the SID and the SOD corresponds to the thickness of the subject. The SID may be stored in the storage 160 in advance as a default value, or alternatively, may be calculated based on the location of the X-ray source 110 moving along the guide rail 30 and a fixed location of the install part 14, 24.

A screen is displayed to guide designation of a region of interest, in 323, and when designation of the region of interest is received from the user, in 324, the COR is determined based on the region of interest, in 325. This is the same as what is described in the embodiment of FIG. 19.

Figure 22:
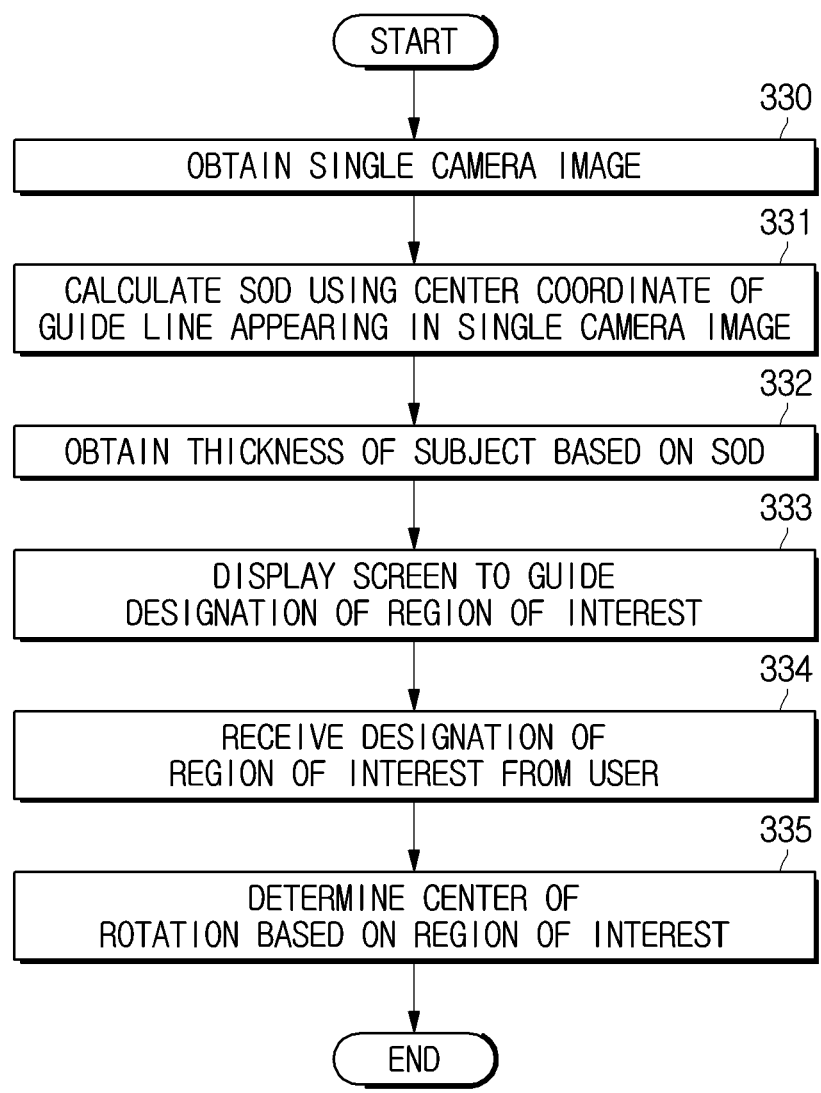
FIG. 22 is a flowchart of an instance of obtaining an SOD using a single camera in a control method of an X-ray imaging apparatus, according to an embodiment of the present disclosure.

FIG. 22 is a flowchart of an instance of obtaining an SOD using a single camera in a control method of an X-ray imaging apparatus, according to an embodiment of the present disclosure.

Referring to FIG. 22, a single camera image is obtained in 330. The guide line GL appears in the camera image $I_{ca}$ taken by the single camera 122, and the COG may be assumed to be the center on the xy-plane of the X-raying portion.

An SOD is calculated using center coordinates of the guide line appearing in the single camera image, in 331. A correlated image I_CO to the guide line GL of the camera image I_CA may be obtained using template matching. By using the maximum value of the correlated image, the center point $x_R$ of the guide line GL is obtained from the camera image I_CA. The storage 160 may formulate and store a relation between camera parameters, the center point of the guide line appearing in the camera image, and the SOD. Accordingly, the SOD may be obtained by applying the obtained center point $x_R$ to the equation 2.

The process of calculating the SOD using the single camera image may be performed by the controller 130 or by the single camera 122.

Thickness of the subject is obtained based on the SOD, in 332. The controller 130 may calculate thickness of the subject in a way of subtracting the SOD from the SID.

A screen is displayed to guide designation of a region of interest, in 333, and when designation of the region of interest is received from the user, in 334, the COR is determined based on the region of interest, in 335. This is the same as what is described in the embodiment of FIG. 19.

Figure 23:
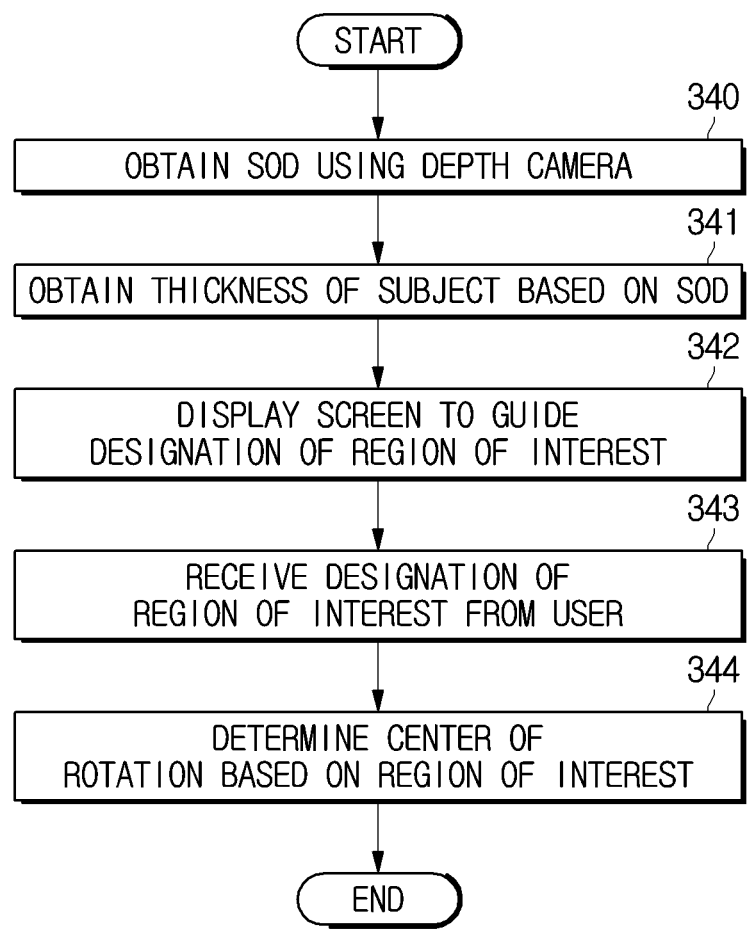
FIG. 23 is a flowchart of an instance of obtaining an SOD using a depth camera in a control method of an X-ray imaging apparatus, according to an embodiment of the present disclosure.

FIG. 23 is a flowchart of an instance of obtaining an SOD using a depth camera in a control method of an X-ray imaging apparatus, according to an embodiment of the present disclosure.

Referring to FIG. 23, an SOD is obtained using a depth camera, in 340. For example, the depth camera may include an infrared sensor and a color camera to acquire the depth information of a subject. An SOD may be included in a depth image output by the depth camera, and the controller 130 may obtain the SOD from the depth image.

Thickness of the subject is obtained based on the SOD, in 341. The controller 130 may calculate thickness of the subject in a way of subtracting the SOD from the SID. The SID may be stored in the storage 160 in advance as a default value, or calculated by the controller 130 based on the location of the X-ray source 110 moving along the guide rail 30 and a fixed location of the install part 14, 24, or obtained from the depth image.

A screen is displayed to guide designation of a region of interest, in 342, and when designation of the region of interest is received from the user, in 343, the COR is determined based on the region of interest, in 345. This is the same as what is described in the embodiment of FIG. 19.

Figure 24:
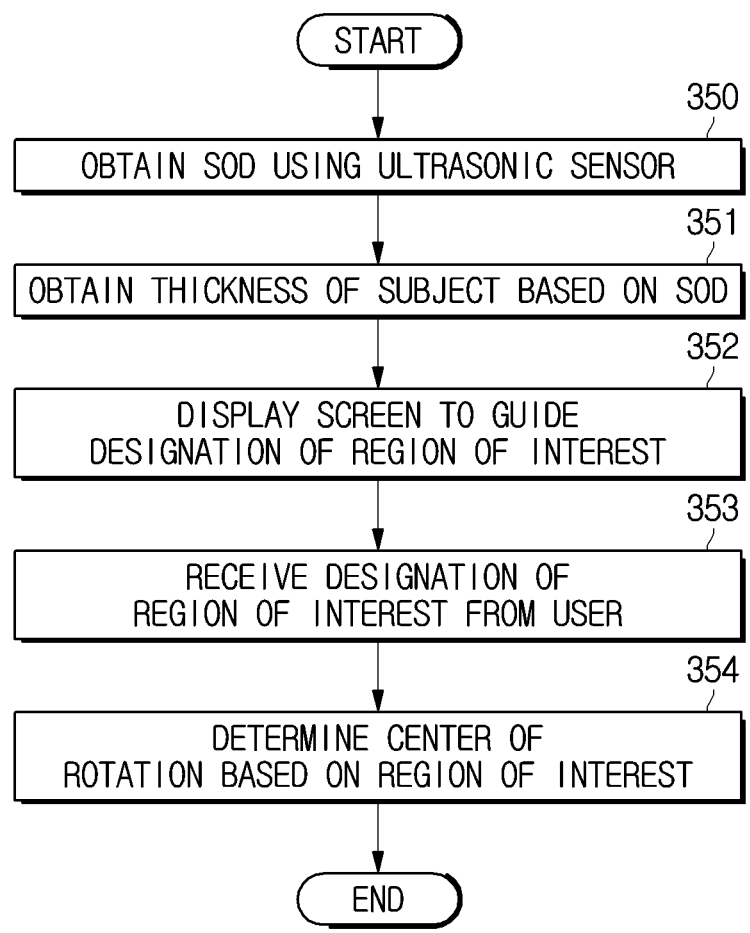
FIG. 24 is a flowchart of an instance of obtaining an SOD using a distance measurement sensor in a control method of an X-ray imaging apparatus, according to an embodiment of the present disclosure.

FIG. 24 is a flowchart of an instance of obtaining an SOD using a distance measurement sensor in a control method of an X-ray imaging apparatus, according to an embodiment of the present disclosure.

In an embodiment of the control method of the X-ray imaging apparatus, an SOD may be obtained by employing not only the aforementioned single camera, stereo camera, and/or depth camera but also various sensors used to measure a distance to an object.

Referring to FIG. 24, an SOD is obtained using an ultrasonic sensor, in 350. In this case, the sensor 120 may employ the ultrasonic sensor which includes a transmitter for transmitting ultrasounds and a receiver for receiving ultrasounds reflecting off the subject and returning. The ultrasonic sensor may measure a distance to the subject, i.e., the SOD, by using time for which the ultrasound reflects off and returns to the receiver and the traveling speed of the ultrasound.

Alternatively, a photo sensor including an emitter and a receptor may be employed to calculate the distance SOD based on the time for which the light irradiated from the emitter reflects off the subject and returns, or by measuring an amount of the light returning off from the subject or by using triangulation.

Thickness of the subject is obtained based on the SOD, in 351. The controller 130 may calculate thickness of the subject in a way of subtracting the SOD from the SID.

A screen is displayed to guide designation of a region of interest, in 352, and when designation of the region of interest is received from the user, in 344, the COR is determined based on the region of interest, in 353. This is the same as what is described in the embodiment of FIG. 19.

In the embodiments of FIGS. 20 to 24, the SID is stored in advance, or the controller 130 is able to calculate the SID from information stored in advance. However, in an occasion when the SID may not be figured out because e.g., the X-raying is performed in the portable mode, as in the embodiment in connection with FIG. 12, the stereo camera image or the single camera image is obtained in both conditions where the subject P is placed on the X-ray detector 200 and where the subject P is not placed on the X-ray detector 200, thereby obtaining not only the SOD but also the SID.

Alternatively, it is also possible to obtain the thickness of the subject by using a distance between a plurality of indicators by having the plurality of indicators, such as both hands contained in one camera image as in the aforementioned embodiment in connection with FIGS. 13 and 14. One of the plurality of indicators may be located on the front face of an X-raying portion of the subject P, and the other may be located at a distance of the thickness of the X-raying portion away from the front face (i.e., at a position of the X-ray detector).

In a case that a distance measurement sensor, such as a photo sensor, an ultrasonic sensor, etc., is used, a distance to the X-ray detector 200 may further be measured separately to obtain the SID.

Figure 25:
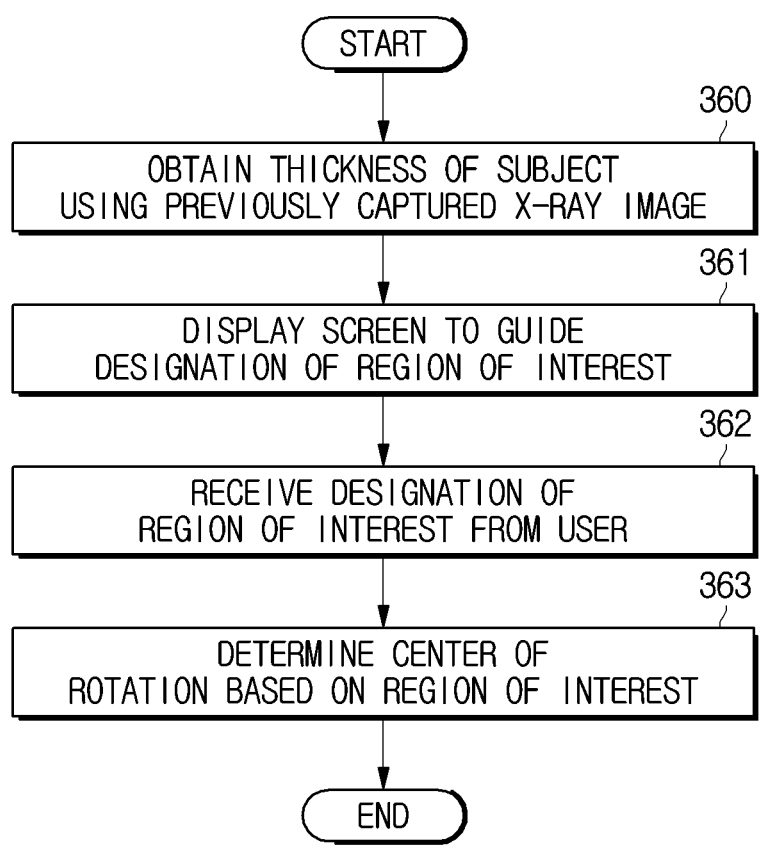
FIG. 25 is a flowchart of an instance of using a previously captured X-ray image in a control method of an X-ray imaging apparatus, according to an embodiment of the present disclosure.

FIG. 25 is a flowchart of an instance of using a previously captured X-ray image in a control method of an X-ray imaging apparatus, according to an embodiment of the present disclosure.

Referring to FIG. 25, thickness of the subject is obtained using a previously captured X-ray image, in 360. The previous X-ray image 152b may be a tomogram taken with the same protocol for the same patient. For example, if a follow-up test is to be performed or if retaking is to be performed because a lesion suspicious area is found, the previous X-ray image for the same patient may have been stored in the storage 160. Since the previous X-ray image 152b, which is a tomogram, includes thickness information of the subject, the controller 130 may measure thickness of the subject appearing in the previous X-ray image 152b.

A guide screen is displayed to guide designation of a region of interest, in 361. In the guide screen 152, an SID, an SOD, thickness of the subject (TH), a distance from the X-ray source 110 to the COR ($D_{COR}$) may be displayed based on the previous X-ray image 152b.

Designation of a region of interest is received from the user, in 353. The user may apply the distance to COR ($D_{COR}$) displayed on the guide screen 152 as it is or may change the distance. For example, in the case of applying the displayed distance to COR ($D_{COR}$) as it is, a stay button 152c-1 may be selected, and in the case of changing the distance to COR ($D_{COR}$) as shown in FIG. 19, a region of interest is designated in the previous X-ray image 152b and a change button 152c-2 may be selected.

A COR is determined based on the region of interest, in 354. When the user designates a region of interest, the controller 130 may reset the COR of the X-ray source 110 to be the designated region of interest. Furthermore, the controller 130 may recalculate a distance to the COR ($D_{COR}$) based on the changed COR and the display 150 may reflect the recalculated information.

The display 150 may display the new COR on the guide screen 152 and update the distance from the X-ray source 110 to the COR ($D_{COR}$).

If the designation of a region of interest changes not only the position of the COR on the z-axis but also the position of the COR on the xy-plane, the controller 130 may control movement of the X-ray source 110 by reflecting the change.

Once the COR is set, the controller 130 may perform X-raying while linearly moving and rotating the X-ray source 110 based on the set COR, and reconstruct 2D projection images obtained by the X-raying to obtain a tomogram or 3D volume data.

According to the embodiments of the present disclosure, an X-ray imaging apparatus and control method thereof may prevent degradation of the resolution of X-ray images by setting a COR of an X-ray source taking into account thickness of the subject.

Furthermore, an area that the user wants to observe with interest may be shown in an even clearer image by taking into account a region of interest designated by the user as well as the thickness of the subject.

According to embodiments of an X-ray imaging apparatus and control method thereof, occurrence of an error in the center of rotation of an X-ray source and the resultant degradation of resolution in a depth direction may be prevented by measuring exact thickness of a subject and determining the center of rotation taking into account the thickness of the subject and a region of interest designated by the user.

Several embodiments have been described above, but a person of ordinary skill in the art will understand and appreciate that various modifications can be made without departing the scope of the present disclosure. Thus, it will be apparent to those ordinary skilled in the art that the true scope of technical protection is only defined by the following claims.

What is claimed is:

1. An X-ray imaging apparatus comprising:
   an X-ray source configured to irradiate X-rays;
   a sensor configured to obtain a distance between the X-ray source and a subject;
   a display configured to display a graphical object in association with the subject;
   an input configured to receive a designation of a region of interest of the subject through the graphical object displayed on the display; and
   a controller configured to:
   obtain a thickness of the subject based on the distance obtained between the X-ray source and the subject,
   determine a center of rotation to be set for the X-ray source based on the designation of the region of interest of the subject received through the input and the thickness of the subject obtained,
   control a movement of the X-ray source according to the determined center of rotation of the X-ray source, and
   generate a tomogram of the region of interest of the subject using a plurality of X-ray images obtained by controlling the movement of the X-ray source according the center of rotation of the X-ray source.

2. The X-ray imaging apparatus of claim 1, wherein the sensor comprises at least one of a stereo camera, a single camera, a depth camera, a photo sensor, an ultrasonic sensor, and a laser sensor.

3. The X-ray imaging apparatus of claim 1, wherein the controller is configured to obtain the thickness of the subject based on the distance between the X-ray source and the subject and a distance between the X-ray source and an X-ray detector.

4. The X-ray imaging apparatus of claim 3, wherein the distance between the X-ray source and the X-ray detector is detected by the sensor.

5. The X-ray imaging apparatus of claim 1, wherein the display is configured to display the distance between the X-ray source and the subject and the thickness of the subject.

6. The X-ray imaging apparatus of claim 1, wherein the display is configured to display the graphical object in association with the subject to be proportional to the thickness of the subject.

7. The X-ray imaging apparatus of claim 6, wherein the controller is configured to determine a position of the region of interest in a direction of thickness based on a relationship between a designated position of the region of interest on the graphical object and the thickness of the subject, and determine the determined position in the direction of thickness as the center of rotation.

8. The X-ray imaging apparatus of claim 1, wherein the controller is configured to set a center of the subject in a direction of thickness to be the center of rotation of the X-ray source, before the designation of the region of interest, and
wherein the display is configured to display information regarding a position of the set center of rotation of the X-ray source on the graphical object.

9. The X-ray imaging apparatus of claim 1, wherein the display is configured to display a previously captured tomogram of the subject as the graphical object.

10. The X-ray imaging apparatus of claim 1, wherein the X-ray source comprises a collimator configured to adjust an X-ray irradiation area and a collimator lamp configured to irradiate visible rays into the adjusted X-ray irradiation area.

11. The X-ray imaging apparatus of claim 10, wherein the sensor is further configured to obtain a camera image having a guide line formed by the visible rays marked on the subject.

12. The X-ray imaging apparatus of claim 11, wherein the sensor is configured to obtain a correlated image using template matching, determine a position of a center of the guide line in the camera image based on the correlated image, and obtain the distance between the X-ray source and the subject based on the position of the center of the guide line.

13. A control method of an X-ray imaging apparatus, the method comprising:
obtaining a thickness of a subject;
displaying a graphical object in association with the subject;
receiving a designation of a region of interest of the subject through the graphical object displayed by the displaying;
determining a center of rotation to be set for an X-ray source based on the designation of the region of interest and the thickness of the subject obtained;
controlling a movement of the X-ray source according to the center of rotation of the X-ray source; and
generating a tomogram of the region of interest of the subject using a plurality of X-ray images obtained by controlling the movement of the X-ray source according the center of rotation of the X-ray source.

14. The control method of claim 13, wherein the obtaining of the thickness of the subject comprises using a sensor including at least one of a stereo camera, a single camera, a depth camera, a photo sensor, an ultrasonic sensor and a laser sensor to obtain the distance between the X-ray source and the subject.

15. The control method of claim 14, wherein the thickness of the subject is obtained based on the distance between the X-ray source and the subject and a distance between the X-ray source and an X-ray detector.

16. The control method of claim 14, further comprising:
displaying the distance between the X-ray source and the subject and the thickness of the subject.

17. The control method of claim 13, wherein the displaying of the graphical object in association with the subject comprises displaying the graphical object to be proportional to the thickness of the subject.

18. The control method of claim 17, wherein the determining of the center of rotation of the X-ray source comprises determining a position of the region of interest in a direction of thickness based on a relationship between the position of the region of interest which is designated on the graphical object and the thickness of the subject, and determining the determined position in the direction of thickness as the center of rotation.

19. The control method of claim 13, further comprising:
setting a center of the subject in a direction of thickness to be the center of rotation of the X-ray source, before the designation of the region of interest; and
displaying information regarding a position of the set center of rotation of the X-ray source on the graphical object.

20. The control method of claim 13, wherein the graphical object displayed in association with the subject comprises a previously captured tomogram of the subject.

* * * * *